United States Patent
Lukac et al.

(10) Patent No.: US 10,518,299 B2
(45) Date of Patent: Dec. 31, 2019

(54) CLEANING SYSTEM AND METHOD FOR OPERATING THE CLEANING SYSTEM

(71) Applicant: Fotona d.o.o, Ljubljana (SI)

(72) Inventors: Nejc Lukac, Ljubljana (SI); Matjaz Lukac, Ljubljana (SI); Matija Jezersek, Radomlje (SI); Peter Gregorcic, Ljubljana (SI)

(73) Assignee: FOTONA D.O.O., Ljubljana (SI)

( * ) Notice: Subject to any disclaimer, the term of this patent is extended or adjusted under 35 U.S.C. 154(b) by 55 days.

(21) Appl. No.: 15/227,068

(22) Filed: Aug. 3, 2016

(65) Prior Publication Data
US 2017/0036253 A1     Feb. 9, 2017

(30) Foreign Application Priority Data
Aug. 3, 2015 (EP) .................................... 15002308

(51) Int. Cl.
  *B08B 7/02* (2006.01)
  *A61L 2/00* (2006.01)
  (Continued)

(52) U.S. Cl.
  CPC .............. *B08B 7/02* (2013.01); *A61B 18/26* (2013.01); *A61L 2/0029* (2013.01); *B08B 3/102* (2013.01);
  (Continued)

(58) Field of Classification Search
  None
  See application file for complete search history.

(56) References Cited

U.S. PATENT DOCUMENTS 5,116,227 A      5/1992  Levy
6,086,366 A  *   7/2000  Mueller ............... A61C 1/0046
                                                    433/29
(Continued)

FOREIGN PATENT DOCUMENTS

EP         2 907 471 A1    8/2015
WO     WO 99/16366 A1      4/1999
(Continued)

OTHER PUBLICATIONS

European Search Report, Appl. No. EP 15002308, dated Feb. 11, 2016, 9 pgs.

*Primary Examiner* — Katelyn B Whatley
(74) *Attorney, Agent, or Firm* — Paul D. Strain, Esq.; Strain & Strain PLLC

(57) ABSTRACT

The application relates to a cleaning system configured for cleaning of cavities filled with a liquid, including fragmentation, debridement, material removal, irrigation, disinfection, and decontamination. The cleaning system includes an electromagnetic radiation system and a liquid. A treatment handpiece irradiates the liquid within a cavity with a radiation beam, producing a first vapor bubble using first pulse, and, at a different location, a second vapor bubble using a second pulse. The pulse repetition time is adjusted to ensure efficacy, for example such that an onset time of the second vapor bubble is within the first contraction phase of the first vapor bubble, when the first vapor bubble has contracted from its maximal volume to a size in a range from about 0.7 to about 0.1 of the maximal volume.

30 Claims, 10 Drawing Sheets

(51) Int. Cl.
  *B08B 3/10*    (2006.01)
  *A61B 18/26*   (2006.01)
  *A61B 18/00*   (2006.01)

(52) U.S. Cl.
  CPC ........... *A61B 2018/00404* (2013.01); *A61B 2018/00505* (2013.01); *A61B 2018/263* (2013.01); *A61L 2202/11* (2013.01); *A61L 2202/17* (2013.01)

(56) References Cited

U.S. PATENT DOCUMENTS

| | | |
|---|---|---|
| 2003/0136756 A1 | 7/2003 | Leclair |
| 2004/0020905 A1 | 2/2004 | Song et al. |
| 2009/0000665 A1* | 1/2009 | Oshemkov ............. A61B 18/26 137/13 |
| 2009/0220908 A1 | 9/2009 | Divito et al. |
| 2013/0084545 A1* | 4/2013 | Netchitailo ............. A61O 5/02 433/224 |

FOREIGN PATENT DOCUMENTS

| | | |
|---|---|---|
| WO | WO 2008/149352 A2 | 12/2008 |
| WO | WO 2013/049832 A2 | 4/2013 |
| WO | WO 2013/169181 A1 | 11/2013 |

\* cited by examiner

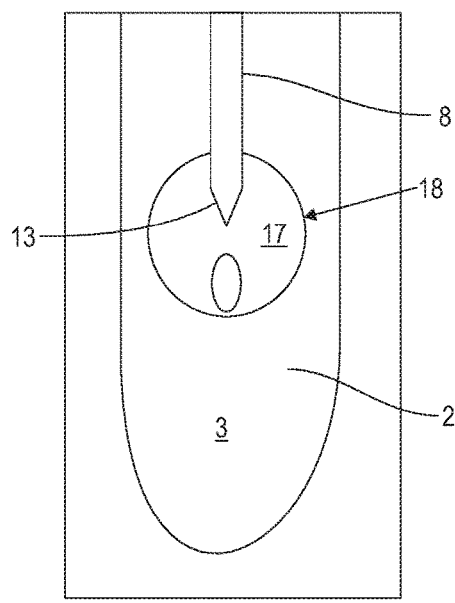 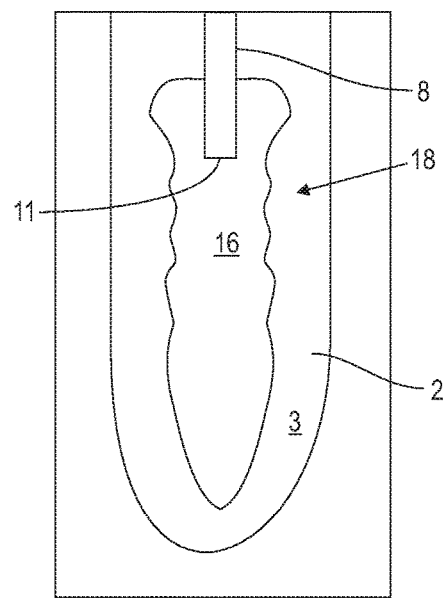
*Fig. 5a*        *Fig. 5b*

CLEANING SYSTEM AND METHOD FOR OPERATING THE CLEANING SYSTEM

CROSS-REFERENCE TO RELATED PATENT APPLICATIONS

This application is based upon and claims the benefit of priority from prior European Patent Application No. 15 002 308.3, filed Aug. 3, 2015, the entire contents of which are incorporated herein by reference in their entirety.

TECHNICAL FIELD

The present invention relates to a cleaning system for cleaning, including debridement, material removal, irrigation, disinfection and decontamination of surfaces of cavities filled with a liquid, and for fragmenting particles within such cavities, according to the preamble of claim 1, and a method for operating the cleaning system.

BACKGROUND

When energy is locally deposited within a liquid, for example with an intense focused electromagnetic radiation (e.g., laser light) or with an electrical discharge through a spark, locally induced boiling of the liquid leads to a creation of a cavitation bubble that rapidly expands due to the high pressure within the vapor. When the bubble reaches its maximum volume where the internal pressure is lower than in the surrounding liquid the bubble starts to collapse. When the collapsing bubble reaches a given size it may rebound and the process repeats until there is insufficient energy for the bubble to rebound again. These violent cavitation oscillations lead to rapid streaming of liquid molecules around the cavitation bubble. It is also known that a cavitation bubble collapsing near a boundary forms a liquid jet directed at the boundary. Even more importantly, under appropriate conditions, an intense shock wave may be emitted during the bubble's collapse.

The strong mechanical forces associated with rapid bubble oscillations can break particles or remove particles from the surface, thus locally cleaning it. This effect is of interest for industrial applications, and as well in medicine. Laser-induced cavitation bubbles have been used in ophthalmology, cardiology, urology and dentistry. For example, laser pulses produce plasma with subsequent bubble formation for ocular surgery by photo-disruption. Laser induced lithotripsy fragments kidney stones through cavitation erosion. Laser pulses have been used to remove thrombus in obstructed arteries. In endodontics, laser activated irrigation is used to debride dental root canals. Laser induced cavitation may be also used for cleaning, debriding and disinfection of periodontal pockets, holes created during bone surgery, or surfaces of inserted implants.

In what follows, the terms "liquid" and "fluid" will be used interchangeably; furthermore, the term "cleaning" will be used to describe all or any of the potential mechanical, disinfecting or chemical effects of cavitation oscillations on surrounding environment (e.g., fragmentation, debridement, material removal, irrigation, cleaning, disinfection).

The principle lying behind cavitation phenomena is the difference in compressibility between a gas and a liquid. The volume of liquid hardly changes in response to a variation in pressure, whereas the volume of the gaseous interior of a bubble can change dramatically. Any contraction or expansion of the bubble is inevitably accompanied by a displacement of an equal volume of the much denser surrounding liquid. As a result, strong bubble's response in combination with the compressible interior can provide not only localized fluid motion but also tremendous focusing of the liquid kinetic energy. Of particular interest for cleaning are the shock waves which may form during the bubble's collapse. These shock waves spread through the volume at supersonic speeds, and interact disruptively with the surrounding environment (e.g., cavity walls). These waves are not only very effective in removing any contamination from the cavity surfaces but can also kill bacteria, leading to a partial or complete disinfection of the treated cavity.

In an infinite liquid, a secondary shock wave is emitted during the accelerated contraction of the bubble cavity. This secondary shock wave is to be distinguished from the primary shock wave which is sometimes emitted during the initial bubble expansion phase when laser energy is locally deposited into a liquid within a very short time of nanoseconds or less. In what follows, the term "shock wave" will represent the secondary shock wave emission only.

The (secondary) shock wave emission occurs as follows. At the initial moment of the bubble's contraction, the pressure inside the bubble equals that of the saturated vapor which is much less than the liquid pressure. Because of this transition, the bubble starts to contract and the bubble vapor pressure starts to grow. Initially, the bubble contraction is relatively slow. However, as the pressure rises, this leads to a vapor mass loss due to the condensation process on the bubble surface, accelerating the implosion even further. This ever faster acceleration results in a violent collapse of the bubble, leading to heating up of the vapor and, most importantly, to emission of a supersonic shock wave emanating from the collapsed bubble. And finally, when the vapor temperature reaches its critical value the condensation process stops, which leads to an even faster rise of the vapor pressure until the contraction stops and the bubble begins to rebound.

Whether the shock wave is emitted and with what amplitude depends among other parameters on the properties of the liquid and on the dimensions of the reservoir that contains the liquid. For example, it is known that for liquids with higher viscosity, bubble's oscillations are slower and last longer. In viscous fluids, the dynamics of the collapse is slowed down, reducing the energy of the shock wave. In highly viscous fluids, shock waves are not observed at all.

Similar dependence applies also with regard to the dimensions of the reservoir. In a free liquid, bubble oscillations can be accommodated by displacing the liquid at long distances. However, in a confined environment, a free expansion of the bubble is not possible, and the expansion and contraction of the bubble is slowed down by the added resistance to flow due to the impermeability and the no-slip condition on the reservoir's surface. This process delays the dynamics of bubble's expansion and implosion compared to a free liquid situation, and the period of the bubble's oscillations can be extended up to ten times. More importantly, because of the slowed down dynamics of the bubble's collapse, shock waves are weaker or do not occur at all. The influence of the reservoir's boundaries on the bubble's dynamics and shock wave formation can be roughly evaluated by introducing a containment factor ($\gamma$) representing a ratio, $\gamma=d_r/d_b$, between the smallest dimension of the reservoir ($d_r$) and the maximal dimension of the bubble ($d_b$) in the direction where the reservoir's dimension is smallest. Experiments have shown that the "containment" starts to exert significant influence on the bubble dynamics at containment ratios $\gamma<3$. Typically, at containment ratios $\gamma<2$, shock waves are not observed.

In biomedical applications, bubbles generated by a focused laser light have a typical maximum dimension between about 0.1 and 10 mm. For the purposes of understanding our invention it is important to note that this means that for most typically applied laser parameters and anatomic liquid reservoirs, such as blood vessels, ureter canals, or root canals, the containment factor is such that shock waves are weak or are not emitted at all. The cleaning effect of cavity oscillations is therefore limited to rapid liquid streaming and liquid jets, while the potential of much more violent shock waves is not utilized.

In particular, when performing, for example, dental endodontic treatments, removing debris from root canal surfaces and eliminating infection consists of adding various chemical solvents into a root canal, and then using a prior art laser irrigation method primarily to enhance the spreading of the chemical irrigant into hard to reach root canal areas. The use of potentially toxic irrigants is not desirable, however due to the absence of shock waves when performing prior art methods, using only water as the irrigating liquid is not sufficiently effective for cleaning and disinfecting root canals.

Accordingly, improved methods, techniques and technologies that can improve the cleaning efficacy of cavitation oscillations in small liquid reservoirs are desirable. The liquid reservoir may be a cavity, canal, vessel (e.g., a blood vessel), passage, opening surface which is to be cleaned or disinfected. In what follows the terms reservoir and/or cavity will be used interchangeably to describe any or all of the applicable liquid reservoirs.

Furthermore, with prior methods for cavitation cleaning it remains desirable to provide improved, more effective cleaning devices and/or methods wherein the electromagnetic radiation treatment parameters are adjusted and/or optimized to obtain strong secondary shock waves during bubble cavitation oscillations even in confined geometries (e.g., root canal systems, blood vessels, urinary tracts, periodontal pockets, surgical holes and the like). The material to be removed may include bacteria or debris (e.g., plaque, calculus, dirt, particulate matter, adhesives, biological matter, residue from a cleaning process, dust, stains) located on surfaces of the liquid reservoir, however, in other examples, the bacteria or debris may be suspended within the liquid filling the treated cavity.

The object of the present invention is to provide an improved cleaning system with a better conversion of electromagnetic energy into shock waves for improved cleaning results.

This object is solved by the cleaning system according to claim 1.

A further object of the present invention is to provide a method for operating said cleaning system to achieve improved cleaning results.

This object is solved by the method according to claim 24.

In what follows the terms electromagnetic radiation, light, laser or laser light will be used to describe any source of electromagnetic radiation or any electromagnetic radiation, where the source of the electromagnetic radiation may be a laser, laser diode, diode, lamp or any other source configured to produce the electromagnetic radiation having the wavelength that is substantially absorbed in the liquid, either in a linear or non-linear regime. A substantial or significant absorption means in the context of the present invention any absorption of the electromagnetic radiation energy to such an extent, that bubbles as described below are generated within the liquid. Said substantial or significant absorption covers in particular the interaction of laser light having a wavelength in a range from above 0.4 µm to 11.0 µm inclusive, including both wavelength in the range from about 1.3 µm to about 11.0 µm being highly absorbed in OH containing liquids, and wavelength in the range from about 0.4 µm to about 1.3 µm being weakly absorbed in OH containing liquids. However, any other suitable radiation and wavelength is covered like IPL (Intense Pulse Light) from flashlamp sources, in particular with wavelength above 1.3 microns or in the UV region when focused, as well as green flashlamp or diode light in blood. A further option within the invention is the use of a radiofrequency (RF) radiation source and its RF radiation. Within the scope of the present invention further wavelengths may be contemplated in particular in combination with liquids having added absorption enhancing additives.

For the purposes of describing present invention, the conditions under which a laser light is highly absorbed in a liquid is roughly divided into a linear, or thermal regime, and a non-linear regime. A linear absorption regime applies when laser pulse power density in a liquid is not high enough to result in the ionization or in other non-linear interactions with liquid molecules. Typically, lasers with pulse durations in a microsecond or millisecond range (from one microsecond to about 5000 µs), such as flash-lamp pumped free-generation Er:YAG lasers, operate in a linear regime. In this regime, the intensity I of a laser light exponentially diminishes with distance x within a liquid according to I exp (−kx), where k (in $cm^{-1}$) is a linear absorption coefficient of the liquid at the particular laser wavelength. The absorption coefficient k and the corresponding penetration depth, $l=1/k$, are strongly wavelength dependent. For example, the penetration depth of the Er:YAG laser wavelength of 2.94 µm in water is approximately $10^{-4}$ cm while the penetration depth of the Nd:YAG laser wavelength of 1.064 µm is 1 cm. According to this definition, laser wavelengths with l>1000 µm in the linear regime are defined as "weakly absorbed" wavelengths. For water, and other OH-containing liquids, the applicable range of highly absorbed wavelengths extends from about 1.3 µm, inclusive, to about 11 µm, and the applicable range of weakly absorbed wavelengths extends from about 0.4 µm to 1.3 µm. In another example, when the liquid is blood, the 532-nm wavelength of a frequency doubled Nd:YAG laser, the 585 nm wavelength of the pulsed-dye laser or the 568 nm wavelength of the Krypton laser, are of interest since they are strongly absorbed in blood's oxyhemoglobin, with their k being approximately within 300-500 $cm^{-1}$ range.

At extremely high laser power densities, on the order of about of $10^{10}$-$10^{11}$ $W/cm^2$, an "optical breakdown" as a result of the ionization of liquid molecules may occur, leading to an abrupt increase in liquid's absorption. In this, non-linear regime, a high absorption of laser light is observed even for weakly absorbed wavelengths, i.e., for wavelengths which have a long penetration depth p in the linear regime. Non-linear conditions are typically achieved with high pulse power Q-switched laser beams, with pulse durations ($t_p$) in a nanosecond range (from one nanosecond to about 100 ns), especially when these beams are focused into a sufficiently small volume of the liquid. But other high pulse power lasers with even shorter pulse durations, in the picosecond and femtosecond range, have been used to generate cavitation in liquids as well. It is to be appreciated that when an optical path of a weakly absorbed high pulse power laser beam has a focal point located within a liquid, the beam will propagate within the liquid without being appreciably absorbed until it reaches the focal region where the laser power density becomes sufficiently high for nonlinear effects to occur. It is only at this point that a bubble formation will occur.

When a pulsed laser beam which is highly absorbed in liquids, either in a linear or non-linear regime, is delivered to such a liquid a bubble generation occurs. For laser pulse durations longer than approximately 500 nanoseconds there are no primary shock waves created in the liquid during the bubble expansion. Instead, the energy stored in the bubble is converted into acoustic energy only after the bubble reaches its maximum size ($A_{max1}$), and the difference in pressures forces the bubble to collapse. Therefore, lasers operating in a linear regime are most suitable for performing present invention since more energy for secondary shock wave emission has remained available in the bubble before it starts to collapse. However, present invention can be of benefit also for applications where cavitation is generated with lasers operating in a non-linear regime.

In summary, when a pulsed laser beam which is highly absorbed in a liquid, either in a linear or non-linear regime, is delivered to such a liquid, a bubble oscillation sequence develops with a very short temporal oscillation period ($T_B$) in the range from about 100 μsec to about 1000 μsec. The oscillation is damped and lasts for only a few rebounds due to the bubble's energy being spent for heating, moving and displacing the liquid, and under appropriate conditions, also for emitting shock wave acoustic transients. For the purposes of cleaning it is desirable that as much as possible of the bubble's energy is spent in the emission of violent shock waves during the contraction phases of the bubble's oscillation, and preferably at least during the first bubble's contraction phase when the bubble's energy is still high. However, in highly viscous liquids and/or when the reservoir-bubble containment ratios (γ) are small, more energy is wasted for overcoming viscous damping and/or to fight against the resistance of the water which has to be displaced in the small reservoir. Consequently, the bubble's contraction is slowed down, resulting in a lower amplitude shock wave or no shock wave at all.

A laser system can be configured to deliver the laser light to a liquid in a contact or a non-contact manner. In a contact scenario, the laser light is delivered to the liquid through an exit surface of an optical exit component (e.g., fiber, fiber tip, optical window, lens) which is at least partially submersed into the liquid. The laser light's focus is located at the exit surface of the exit component, and the bubble develops in a contact with the exit surface of the submersed optical exit component.

In a non-contact scenario, the optical exit component is configured to be positioned above the surface of the liquid reservoir, with the laser energy being directed through air and possibly other transparent materials (such as, for example an eye lens in case of ophthalmic applications) into the liquid reservoir. In a non-contact scenario, the beam is substantially focused to a point located bellow the liquid surface by means of an appropriate focusing device, and the resulting bubble does not develop in a contact with the optical exit component.

It is to be appreciated that the contact manner is more suitable for configurations when laser light is absorbed in a linear regime, and the non-contact manner is more suitable for configurations when laser light is absorbed in a non-linear regime. However, either of the delivery manners can be used in a linear or a non-linear regime.

Present invention is based on our discovery that when the energy is delivered to a liquid in a set of a minimum of two individual laser pulses (a prior and a subsequent pulse), follow temporally each other by an appropriate pulse repetition time ($T_p$), the pulse repetition time $T_P$ being the time period from the beginning of one single pulse p to the beginning of the next, subsequent pulse p, a shock wave is emitted by the prior bubble, i.e., the bubble resulting from the prior laser pulse, even in situations when no shock wave is emitted by the bubble when only one laser pulse is delivered to the liquid. This observation is explained by the fact that the liquid pressure exerted on the prior bubble by the expanding subsequent bubble, i.e., the bubble resulting from the subsequent laser pulse, forces the prior bubble to collapse faster, which leads to the emission of a shock wave by the prior bubble.

There are two conditions that need to be fulfilled in order for the above described effect to be observed. The first condition requires that the subsequent bubble starts to develop when the prior bubble is already in its implosion phase, with its size having been reduced from its maximum size ($V_{max1}$) to a size in a range from about $0.7 \times V_{max1}$ to about $0.1 \times V_{max1}$. And secondly, the laser energy of the subsequent pulse must be delivered at a location nearby the prior bubble but not within the prior bubble. In the opposite case, the laser beam of the subsequent pulse will not be initially absorbed in the liquid but shall first pass through the prior vapor bubble and will be absorbed at the prior bubble's wall area generally opposite to the direction of the laser beam. This would result in extending the length of the prior bubble in the direction of laser beam emission, and would therefore shift the bubble's dynamics from the contraction to expansion phase, effectively preventing the formation of a shock wave.

When both laser pulses are focused to the same spot within the liquid, the second condition can be fulfilled only when the subsequent laser pulse is emitted when the prior bubble has already moved sufficiently away from its initial position, i.e., from the point in the liquid where laser energy is being locally absorbed within the liquid. Such movement occurs naturally in contact delivery scenarios where during its contraction phase the bubble separates and moves away from the exit surface of the optical exit component. In one of the embodiments, a highly absorbed wavelength may be delivered into a narrow, tube like reservoir, such as a root canal or a blood vessel, by a submerged fiber or fiber tip. In this configuration, the fluid dynamics has been observed to be such that during its contraction phase the bubble separates from the fiber end and moves away from the fiber. This allows the subsequent bubble to develop at the fiber end separately from the prior bubble, and by its expansion to cause the surrounding liquid to exert pressure on the prior bubble during its contraction.

The bubble may move away from the laser's focal point also in non-contact scenarios, providing that the confined reservoir wall's geometry is asymmetrical with regard to the bubble, and the resulting asymmetrical liquid flow shifts the bubble away from its original expansion position.

In another embodiment, the second condition may be fulfilled by physically moving the fiber to a different position within the liquid during the repetition time of the two laser pulses. In yet another embodiment, it is the laser focal point which may be moved in between the pulses, for example by a scanner.

It is to be appreciated that the invention is not limited to the emission of only two subsequent pulses within a pulse set. A third pulse following a second laser pulse, and fulfilling both conditions, may be delivered resulting in an emission of a shock wave by the previous (second) bubble. Similarly, an $n^{th}$ subsequent laser pulse will result in an emission of a shock wave by the $(n-1)^{th}$ bubble, and so on as further laser pulses are being added to the set of pulses. The more laser pulses are delivered in one pulse set, the higher is the laser-to-shock wave energy conversion, with the energy conversion efficiency being proportional to the ratio $(n-1)/n$ where n is the total number of laser pulses delivered in a pulse set. Additionally, repetitive cavitations and shock wave emissions generate an ever increasing number of longer persisting gas (e.g., air) micro-bubbles within a liquid. These micro-bubbles compress and expand under the influence of cavitation oscillations and shock waves, and thus improve the overall cleaning efficacy by contributing to the high-speed fluid motion.

Our experiments show that the separation between the two laser pulses $(T_p)$ should not deviate substantially from the optimal separation $(T_{p\text{-}opt})$ in order for the shock wave to occur. The optimal repetition time $(T_{p\text{-}opt})$ is the pulse repetition time where the subsequent bubble starts to develop when the prior bubble has already contracted to a size in a range from about $0.7 \times V_{max1}$ to about $0.1 \times V_{max1}$, preferably in a range from about $0.5 \times V_{max1}$ to about $0.1 \times V_{max1}$, and expediently in a range from about $0.5 \times V_{max1}$ to about $0.2 \times V_{max1}$. When the same laser device is intended to be used for cleaning differently sized cavities, containing different liquids, and with different laser parameters, this poses a challenge since the bubble oscillation time $(T_B)$, and consequently the required pulse repetition time $(T_{p\text{-}opt})$ depends critically on these conditions, being longer for higher laser pulse energies and pulse durations, more viscous liquids and smaller reservoirs.

In one of the embodiments of our invention, the laser system comprises a feedback system to determine a bubble oscillation dimension or amplitude of the prior vapor bubble generated within the liquid. Furthermore, the laser system comprises adjusting means for adjusting the pulse repetition time $T_p$ to achieve at least approximately that the subsequent bubble, i.e., the bubble generated by the subsequent laser pulse, starts to expand when the prior bubble has already contracted to a size in a range from about $0.7 \times V_{max1}$ to about $0.1 \times V_{max1}$, preferably in a range from about $0.5 \times V_{max1}$ to about $0.1 \times V_{max1}$, and expediently in a range from about $0.5 \times V_{max1}$ to about $0.2 \times V_{max1}$. The feedback system preferably comprises an acoustical, a pressure, or an optical measurement sensor for sensing the bubble size A. As a result of the bubble oscillation sensing, the laser pulse repetition time $T_p$ might be manually adjusted by the user to be approximately equal to $T_{popt}$. However, in a preferred embodiment, the feedback system and the adjusting means are connected to form a closed control loop for automatically delivering a subsequent laser pulse at the moment when the feedback system has detected that the size of the prior bubble has contracted to a size in a range from about $0.7 \times V_{max1}$ to about $0.1 \times V_{max1}$, preferably in a range from about $0.5 \times V_{max1}$ to about $0.1 \times V_{max1}$, and expediently in a range from about $0.5 \times V_{max1}$ to about $0.2 \times V_{max1}$.

In yet other embodiments of the present invention, the laser system is configured to deliver laser energy in innovative "SWEEP" pulse sets wherein the pulse repetition time $T_p$ is "swept" within each pulse set or from pulse set to pulse set across a sufficiently large range of pulse repetition time values $(T_p)$ that the optimal pulse repetition time $(T_{p\text{-}opt})$ is reached at least once during each sweep. In an alternative SWEEP mode the electromagnetic radiation system and/or its operating method are adjusted to generate and deliver multiple pairs of two pulses, and wherein from pair of pulses to pair of pulses the pulse energy of each second pulse is varied in a sweeping manner.

More generally, various shortcomings of prior medical devices and methods (for example, endodontic treatments) can be addressed by utilizing a medical and dental treatment system or other exemplary system configured in accordance with principles of the present disclosure. Outside of the medical and dental fields, control of bacteria or other undesirable matter, such as dirt, particulate matter, adhesives, biological matter, residues, dust and stains, in various systems is also important. Further, cleaning and removal of various materials from surfaces and openings may be required for aesthetic or restoration reasons.

For following the above mentioned inventive findings, the individual pulses as they are known in the prior art are in a preferred embodiment replaced by inventive pulse sets. The individual pulses are combined to pulse sets consisting of a minimum of two and maximally 20 individual pulses, with the intra-set pulse repetition times in the range from 50 μsec to 900 μsec, and the pulse sets being temporally separated from each other by at least 10 ms.

The proposed laser system and method may be applied to any kind of human or animal cavity, or even industrial cavity.

BRIEF DESCRIPTION OF THE DRAWINGS

Embodiments of the invention will be explained in the following with the aid of the drawing in more detail. With reference to the following description, appended claims, and accompanying drawings:

FIG. 5a illustrates an exemplary vapor bubble in generally spherical form;

FIG. 5b illustrates an exemplary vapor bubble in generally elongate form;

DETAILED DESCRIPTION OF PREFERRED EMBODIMENTS

Figure 1:
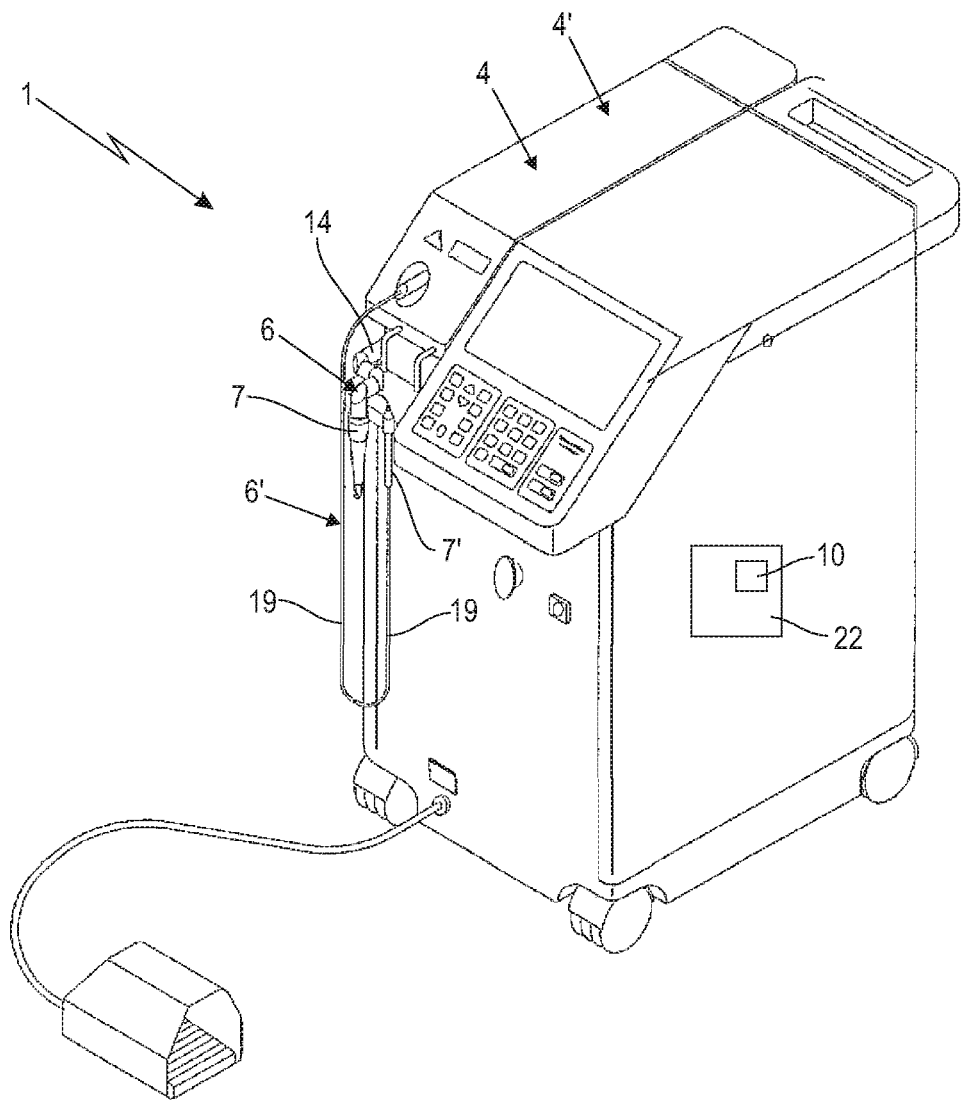
FIG. 1 illustrates an exemplary inventive laser system with both an optical fiber laser delivery system and an articulated arm laser delivery system.

With reference now to FIG. 1, in various embodiments, an electromagnetic radiation system comprising a radiation source for generating a radiation beam is shown. In the following, both the inventive electromagnetic radiation system and an inventive method of operating said electromagnetic radiation system are described. In the shown preferred embodiment, the electromagnetic radiation system is a laser system 1, wherein the radiation source is a laser source 4, and wherein the radiation beam is a laser beam 5. The shown medical treatment laser system 1 comprises at least one laser source 4 for generating a laser beam 5 (FIGS. 4a and 4b), and an optical delivery system 6 for the laser beam 5. The laser system further comprises a schematically indicated control unit 22 for controlling the laser beam 5 parameters, wherein the control unit 22 includes again schematically indicated adjusting means 10 for adjusting the laser beam 5 parameters as described below. The optical delivery system 6 preferably includes an articulated arm 14 and a treatment handpiece 7, wherein the laser beam 5 is transmitted, relayed, delivered, and/or guided from the laser source 4 through the articulated arm 14 and the handpiece 7 to a target. The articulated arm 14 might preferably be an Optoflex® brand articulated arm available from Fotona, d.o.o. (Slovenia, EU). In the shown preferred embodiment a second laser source 4' and a second optical delivery system 6' with a second handpiece 7' is provided, wherein instead of the articulated arm a flexible elongated delivery fiber 19 for guiding the laser beam 5' is incorporated. Despite both laser sources 4, 4' and delivery systems 6, 6' being shown in combination, one of both in the alternative may be provided and used within the scope of the present invention. In this description, the expression medical laser system is sometimes used, meaning both, medical and dental laser systems. Moreover, the medical treatment laser system 1 may be configured with any appropriate components and/or elements configured to facilitate controlled application of laser energy, for example, in order to create vapor bubbles in a liquid 3 within an anatomical cavity 2 for cleaning, including fragmentation, debridement, material removal, irrigation, disinfection and decontamination of said anatomical cavity 2, as shown and described below. However, the invention including the here described inventive device and the inventive method are not limited to cleaning anatomical of body cavities 2. Within the scope of the invention any other cavity 2 like industrial or machinery cavities may be cleaned as well.

It is to be understood that in order to perform cleaning according to the invention, the treated cavity 2 (FIGS. 2, 3) must be filled with a liquid 3. In case of medical or dental applications the cavity 3 may be filled spontaneously with blood or other bodily fluids by the body itself. Alternatively, the cavity may be filled with water, or other liquids such as disinfecting solutions, by the operator. In yet another embodiment, the system may be designed to include a liquid delivery system 26 configured to fill the volume of the cavity with the liquid. Preferably, said liquid 3 is an OH-containing liquid, for example a liquid with its major portion being water. In other examples, the liquid 3 may include abrasive materials or medication, such as antibiotics, steroids, anesthetics, anti-inflammatory medication, antiseptics, disinfectants, adrenaline, epinephrine, astringents, vitamins, herbs, and minerals. Furthermore, the liquid 3 may contain an additive enhancing the absorption of introduced electromagnetic radiation.

Figure 9:
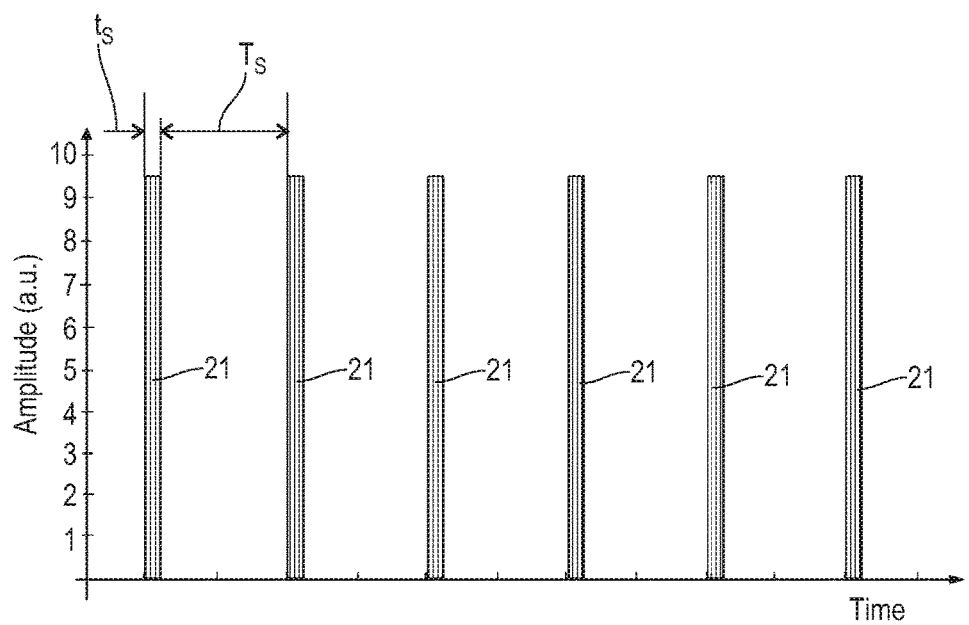
FIG. 9 represents a diagrammatic illustration of the temporal course of pulse sets in accordance with various embodiments of the invention.
Figure 10:
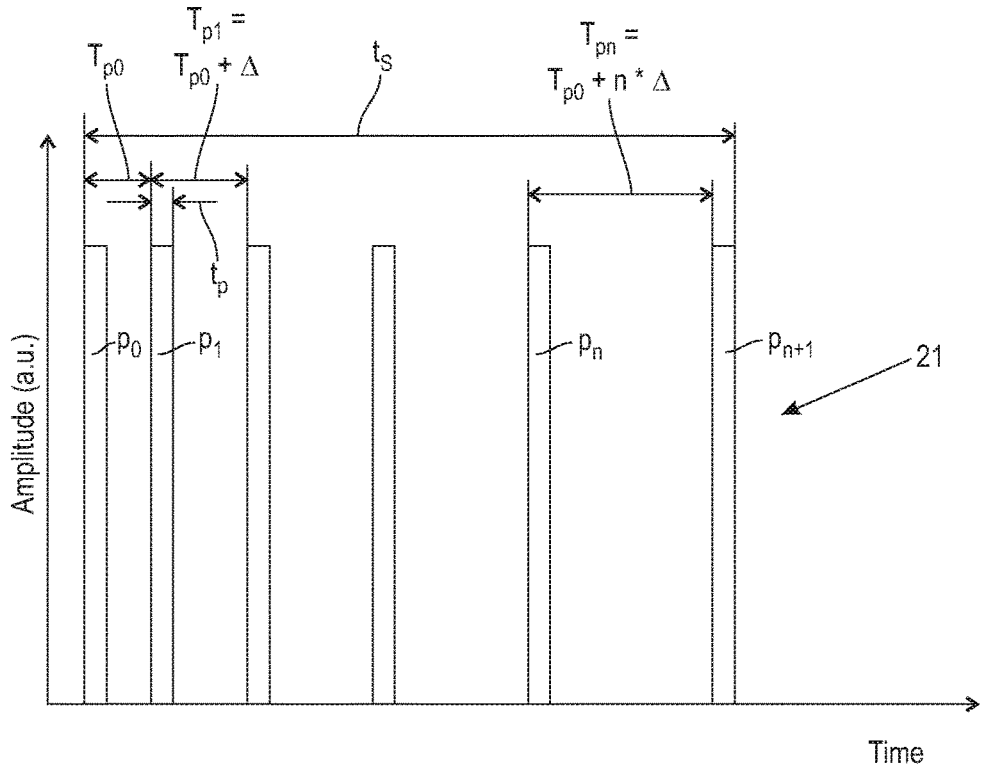
FIG. 10 represents an enlarged diagrammatic illustration of a detail of a pulse set according to FIG. 9 with the temporal course of individual pulses with sweeping pulse repetition rates from pulse to pulse within one pulse set.
Figure 11:
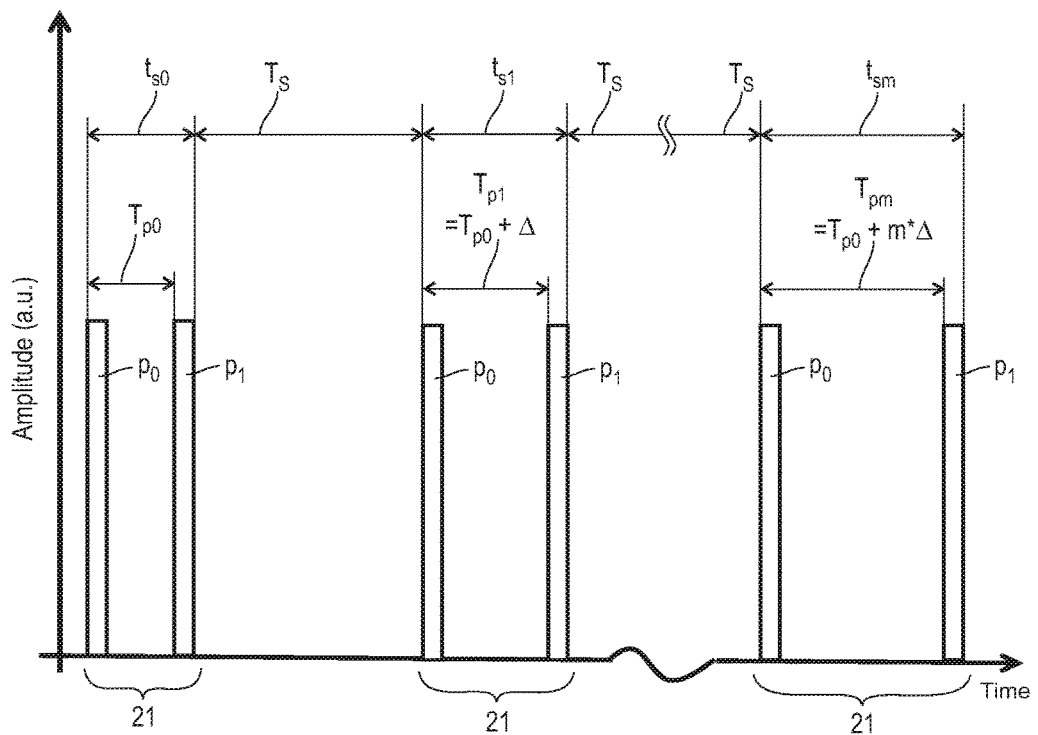
FIG. 11 represents an enlarged diagrammatic illustration of a detail of the temporal course of pulse sets according to FIG. 9 with the temporal course of individual pulses with sweeping pulse repetition rates from pulses to pulse set.

The laser source 4 is a pulsed laser. The laser source 1 may be solid state, and configured with a pulse duration of less than 500 µs. The laser pulse duration is defined as the time between the onset of the laser pulse, and the time when 50% of the total pulse energy has been delivered to the liquid. The pulse duration may be fixed; alternatively, the pulse duration may be variable and/or adjustable. The pulse energy may be fixed; alternatively, the pulse energy may vary during the treatment. The wavelength of the laser beam 5 is in a range from above 0.4 µm to 11.0 µm inclusive. As illustrated in FIGS. 9 to 11, the laser system 1 is adapted to be operated in pulsed operation with pulse sets containing at least two and maximally twenty individual pulses p of a temporally limited pulse duration $t_p$, wherein a temporal separation $T_s$ between the pulse sets is ≥10 ms, and wherein the individual pulses p follow one another with a pulse repetition time $T_p$ within a range of 50 µs, inclusive, to 1000 µs, inclusive The laser source 4, 4' may desirably be configured to generate coherent laser light having a wavelength such that the laser beam 5 is highly absorbed in the liquid 3, wherein the laser pulse duration is in the range of ≥1 µs and <500 µs, and preferably of ≥10 µs and <100 µs. Preferably, the laser source 4, 4' is one of an Er:YAG solid state laser source having a wavelength of 2940 nm, an Er:YSGG solid state laser source having a wavelength of 2790 nm., an Er,Cr:YSGG solid state laser source having a wavelength in a range of 2700 to 2800 nm, an Er:YAlO3 solid state laser having a wavelength of 2690 nm, a Ho:YAG solid state laser having a wavelength of 2100 nm, a $CO_2$ or CO gas laser source having a wavelength of 9000 nm to 10600 nm, all of them providing a laser beam 5 highly absorbed in water and other OH-containing liquids. In particular, the laser source 4, 4' is an Er:YAG laser having a wavelength of 2940 nm, wherein the laser pulse energy is in a range from 1.0 mJ to 100.0 mJ, and preferably within a range from 5.0 mJ to 20.0 mJ.

Other examples of laser sources 4,4' with a laser wavelength highly absorbed in water and other liquids include quadrupled Nd:YAG laser which generates light having a wavelength of 266 nm; an ArF excimer laser which generates light having a wavelength of 193 nm, an XeCl excimer laser which generates light having a wavelength of 308 nm, and a KrF excimer laser which generates light having a wavelength of 248 nm.

In another embodiment, the laser source 4, 4' is one of a frequency doubled Nd:YAG laser source having a wavelength of 532 nm, a dye laser source having a wavelength of 585 nm, or a Krypron laser source having a wavelength of 568 nm, all of them providing a laser beam 5 highly absorbed in oxyhemoglobin within blood vessels. Alternatively, the laser source 4, 4' may desirably be configured to generate coherent laser light having a wavelength such that the laser beam 5 is weakly absorbed in the liquid 3, wherein the laser pulse duration is in the range of ≥1 fs and <100 ns, and preferably of ≥1 ns and <25 ns. Preferably, the laser source 4, 4' is one of a Q-switched Nd:YAG laser source having a wavelength of 1064 nm, a Q-switched ruby laser source having a wavelength of 690 nm, or an alexandrite laser source having a wavelength of 755 nm, including laser sources 4, 4' with frequency doubled wavelengths of these laser sources 4, 4', all of them providing a laser beam 5 weakly absorbed in water and other OH-containing liquids. For such weakly absorbed wavelength the pulse energy of one individual laser pulse p is in the range from 0.05 mJ to 1000 mJ, preferably in the range from 0.5 to 200 mJ, and in particular from 1 mJ to 20 mJ.

Moreover, any other suitable laser source 4, 4' may be utilized, as desired. In certain embodiments, the laser source 1 may be installed directly into the handpiece 7, 7', and no further laser light delivery system 6, 6' such as the articulated arm 14 or elongated delivery fiber 19 is required. Additionally, such handpiece may not be intended to be held in hand but may be built into a table-top or similar device as is the case with laser photo-disruptors for ocular surgery.

Figure 2A:
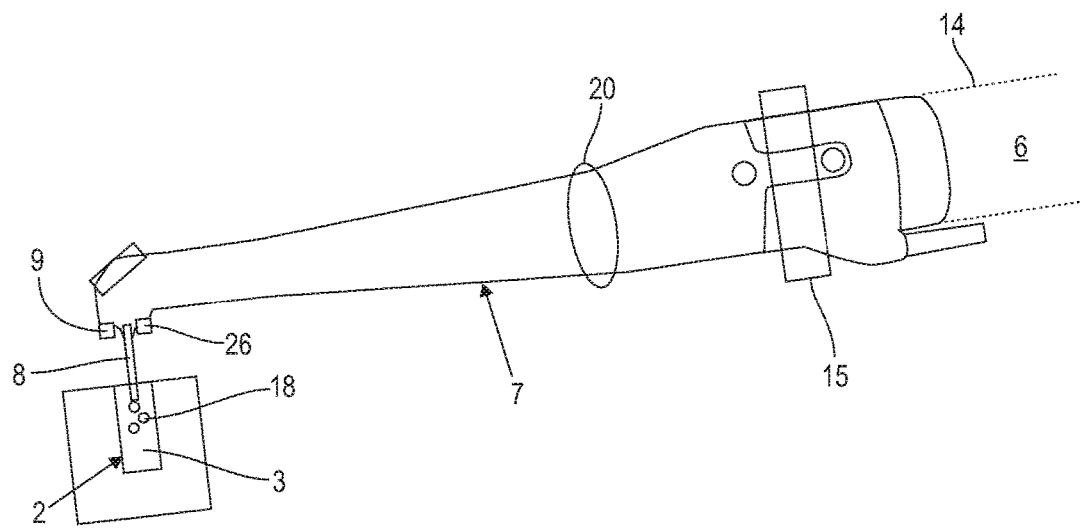
FIG. 2a illustrates an exemplary treatment handpiece fed by an articulated arm in contact operational mode.
Figure 2B:
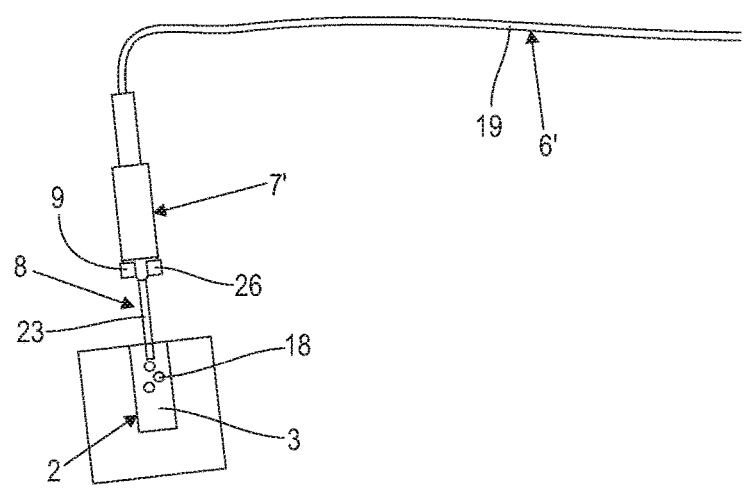
FIG. 2b illustrates an exemplary treatment handpiece fed by a delivery fiber in contact operational mode.

The handpiece 7, 7' includes an exit component 8, through which the laser beam 5 exits the delivery system 6, 6' for entering the liquid 3, as shown in FIGS. 2a, 2b, 3a and 3b. The handpiece 7, 7', and in particular its exit component 8 may be configured to deliver the laser light to the liquid 3 in a contact, and/or non-contact manner. Turning now to FIG. 2a, when the treatment handpiece 7 is configured for a contact delivery, the laser light is from the said "contact" handpiece 7 directed into a "contact" exit component 8 which is configured to be at least partially immersed into the liquid 3 within the treated anatomical cavity 2 in such a manner that the laser light exits the exit component 8 within the liquid 3, at a depth of at least 1 mm, and preferably of at least 3 mm, in order to generate vapor bubbles 18 within the liquid 3, and in order the laser generated vapor bubble(s) 18 to interact with the liquid-to-cavity surface. In various embodiments, the contact exit component 8 may consist of an optical fiber tip as shown in and described along with FIG. 2b and FIG. 3b or a larger diameter exit tip 24 as shown in and described along with FIGS. 4a and 4b. In certain embodiments (FIG. 2a), the treatment handpiece 7 together with a contact exit component 8 comprises H14 tipped laser handpiece model available from Fotona, d.d. (Slovenia, EU). And in certain embodiments, an ending of an elongated delivery fiber 19 of the laser light delivery system 6 may be immersed into the liquid 3, thus serving the function of a contact exit component 8 (FIG. 2b).

For the "contact" scenario as shown in FIGS. 2a and 2b one of the above described highly absorbed or weakly absorbed wavelengths including all other above described parameters is preferably used, thereby generating at least two vapor bubbles 8 within the liquid 3.

In one of the embodiments of our invention, the laser system comprises a feedback system 9 to determine a bubble oscillation dimension or amplitude of the prior vapor bubble 18 generated by the laser beam 3 within the liquid 5. The bubble oscillation intensity development and dynamics are described infra in connection with FIGS. 5 and 6. Furthermore, the laser system comprises adjusting means 10 for adjusting the pulse repetition time $T_p$ to achieve at least approximately that the subsequent bubble, i.e., the bubble generated by the subsequent laser pulse $p_b$, starts to expand when the prior bubble $p_a$ has already contracted to a size in a range from about $0.7 \times V_{max1}$ to about $0.1 \times V_{max1}$, preferably in a range from about $0.5 \times V_{max1}$ to about $0.1 \times V_{max1}$, and expediently in a range from about $0.5 \times V_{max1}$ to about $0.2 \times V_{max1}$ (FIGS. 5 and 7). The feedback system 9 preferably comprises an acoustical, a pressure, or an optical measurement sensor for sensing the oscillating course of the bubble size V. As a result of the bubble oscillation sensing, the laser pulse repetition time $T_p$ might be manually adjusted by the user to be approximately equal to $T_{p\text{-}opt}$. However, in a preferred embodiment, the feedback system 9 and the adjusting means 10 are connected to form a closed control loop for automatically delivering a second laser pulse at the moment when the feedback system has detected that the size of the prior bubble has contracted to a size in a range from about $0.7 \times V_{max1}$ to about $0.1 \times V_{max1}$, preferably in a range from about $0.5 \times V_{max1}$ to about $0.1 \times V_{max1}$, and expediently in a range from about $0.5 \times V_{max1}$ to about $0.2 \times V_{max1}$.

Figure 3A:
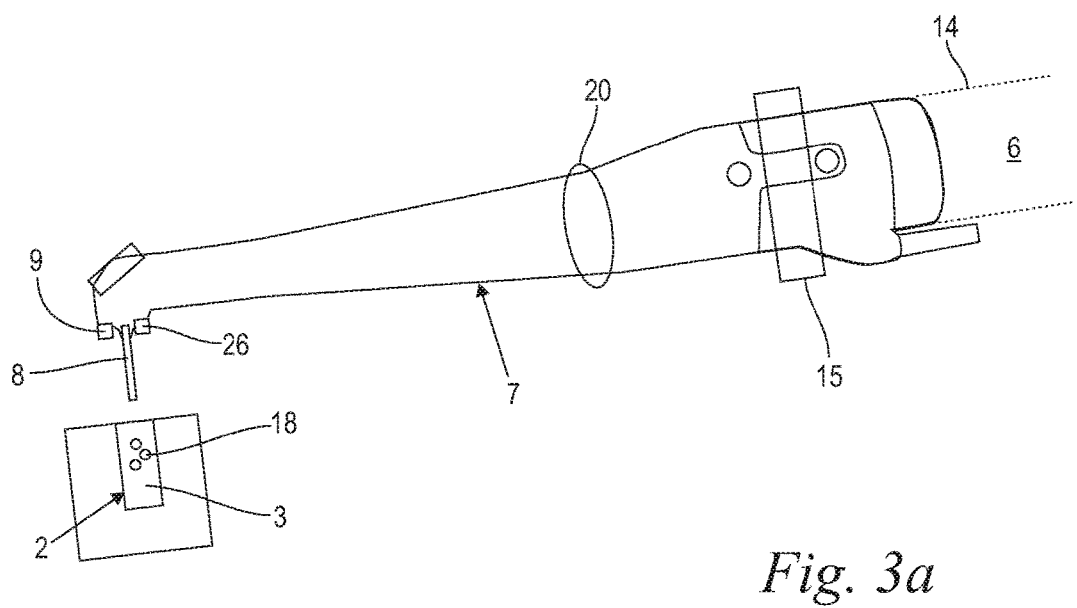
FIG. 3a illustrates an exemplary treatment handpiece fed by an articulated arm in non-contact operational mode.
Figure 3B:
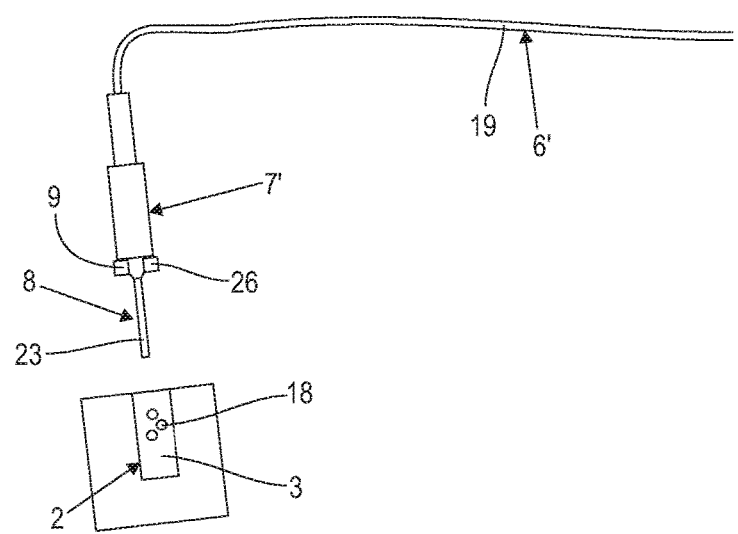
FIG. 3b illustrates an exemplary treatment handpiece fed by a delivery fiber in non-contact operational mode.

When the treatment handpiece 7, 7', and its exit component 8 are configured for a non-contact delivery (FIGS. 3a, 3b), the "non-contact" exit component 8 of the said "non-contact" handpiece 7 is configured to be positioned above the surface of the liquid 3 reservoir, with the laser energy being directed through air and possible other transparent materials (such as, for example an eye lens in case of ophthalmic applications) into the liquid 3 reservoir. In certain embodiments, a laser source 4 with a highly absorbed wavelength might be used as described above, and the exiting laser beam 5 is substantially focused onto the liquid 3 surface. In the shown "non-contact" scenario, however, preferably a laser source 4 with a weakly absorbed wavelength is used as described above, and the beam is substantially focused to a point located bellow the liquid surface by means of an appropriate focusing device, e.g. a lens system 20. The weak absorption allows the laser beam 5 to penetrate the liquid 3 until a certain penetration depth where the focal point is located. In the area of the focal point the laser energy concentration is high enough to generate the desired at least one vapor bubble 18, despite the weak absorption. In certain embodiments (FIG. 3a), non-contact treatment handpiece 7, together with a non-contact exit component 8 comprises H02 tip-less handpiece model available from Fotona, d.d. (Slovenia, EU). And in certain embodiments, an exit component 8 consists of an ending of an elongated laser light delivery fiber 19, which is positioned above the surface of a liquid 3 reservoir (FIG. 3b). Of course, a separate exit component 8 as described along with FIG. 2a might be used for the embodiments of FIGS. 2b, 3a and 3b as well. In yet other embodiments, the exit component 8 may represent a focusing optical system consisting of one or more lenses, such as is the case in ocular surgery photo-disruption procedures.

Moreover, treatment handpiece 7 may comprise any suitable components or elements configured for targeted and/or controllable delivery of laser energy to a liquid 3. Preferably, the laser system 1 comprises a scanner 15 as schematically indicated in FIGS. 2a, 3a, which allows scanning of the exit component 8 cross section with the laser beam 5, as shown in FIGS. 4a, 4b.

Figure 4A:
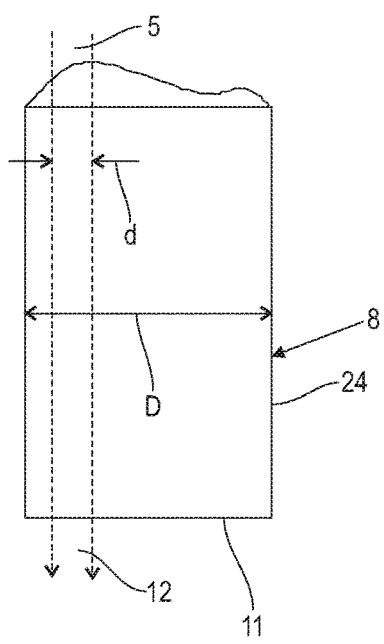
FIG. 4a illustrates an exemplary optical exit component of a treatment handpiece fed by an articulated arm, having a flat tip geometry, and showing the resultant laser beam path.
Figure 4B:
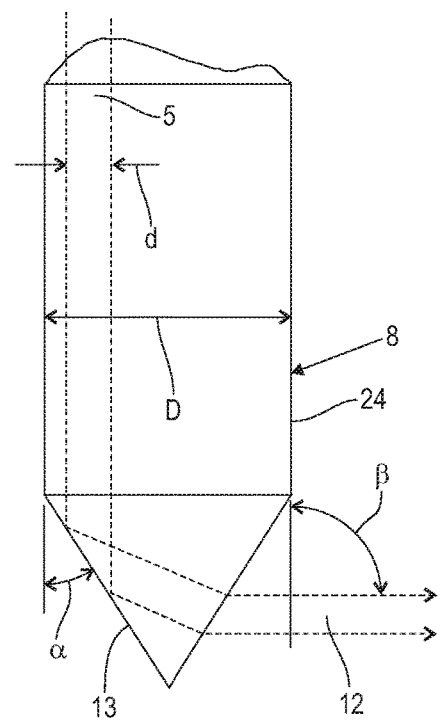
FIG. 4b illustrates an exemplary optical exit component of a treatment handpiece fed by an articulated arm, having a conical tip geometry, and showing the resultant laser beam path.

Turning now to FIGS. 4a and 4b, in various embodiments the exit component 8, preferably but not coercively configured for contact delivery, may consist of an exit tip 24 (FIGS. 4a, 4b) or any other optical element, which extends along a longitudinal axis and is made of a material which is transparent to the laser beam. The exit component 8 preferably has a generally circular cross section, which leads to a generally cylindrical shape. However, any other suitable cross section may be chosen. The exit tip 24 may be of a variety of different shapes (e.g., conical, angled, beveled, double-beveled), sizes, designs (e.g., side-firing, forward-firing) and materials (e.g. glass, sapphire, quartz, hollow waveguide, liquid core, quartz silica, germanium oxide). Further, the exit component 8 may comprise mirrors, lenses, and other optical components.

In one preferred embodiment the exit tip 24 of the exit component 8 has a flat output surface 11 (FIG. 4a). The exit tip 24 of the exit component 8 has a diameter D, while the laser beam 5 has a diameter d. The diameter D of the exit component 8 can be equal to the diameter of the elongated delivery fiber 19 and in particular equal to the diameter d of the laser beam 5. In the embodiment of FIG. 4a, where the exit component 8 is in the form of a larger diameter exit tip 24, the diameter D of the exit component 8 is substantially greater than the diameter d of the laser beam 5. In connection with the a.m. scanner 15 a certain scanning pattern on the flat output surface 11 can be achieved, thereby generating exiting beam portions 12 and as a result vapor bubbles 18 at corresponding locations within the liquid 3 (FIGS. 2a, 3a), as may be desired.

In another embodiment as shown in FIG. 4b, the exit component 8, again in the form of a larger diameter exit tip 24, has a conically shaped output surface 13 being disposed around the longitudinal axis and having an apex facing away from the incoming beam section, wherein the conically shaped output surface 13 has a half opening angle α being adapted to provide partial or preferably total reflection of the incoming beam section into a reflected beam section within the exit component 8 and to provide refraction of the reflected beam section into an exiting beam portion 12 emerging from the exit component 8 through the conically shaped output surface 13 in approximately radial direction relative to the longitudinal axis. In various embodiments, the angle β is expediently in the range 60°≤β≤120°, and preferably about 90°.

Typically, when fiber tips 23 are used, the laser beam 5 extends substantially across the whole cross section of the fiber tip 23. This will result in a circumferentially spread exiting beam portion 12. In certain embodiments, however, as shown in FIG. 4b, the exit component 8 may have a diameter D substantially larger than the diameter d of the laser beam 5, providing space for the laser beam to be scanned over the exit component's conical output surface 13. In such embodiments, the exit component 8 base is preferably of a cylindrical shape. However, any other suitable 3D shape, such as a cube, cuboid, hexagonal prism or a cone, can be used. Scanning the conical output surface 13 with the incoming laser beam 5 allows for generation of multiple exiting beam portions 12 and corresponding vapor bubbles located circumferentially around the exit component 8. Since more than one laser pulse p, i.e. a synchronized train of pulses p (FIGS. 8a to 11) needs to be delivered to the same spot, one could deliver one pulse p exiting beam portion 12 to a related vapor bubble 18 spot, then move to the next vapor bubble 18 spot on the circumference, and so on, and then return to the same initial vapor bubble 18 spot just in time for the next pulse p within the pulse train. This would enable faster procedures since the laser repetition rate would not be limited by the bubble oscillation period $T_B=(t_{min1}-t_{01})$ (FIG. 6) but by the maximum repetition rate of the laser system 1.

With reference now to FIGS. 4a, 4b, in accordance with various embodiments, when laser energy is delivered into a highly absorbing liquid 3 through an exit component 8 having a flat output surface 11 (FIG. 4a), that is immersed into the liquid 3, the above described vapor bubble 18 turns into a channel-like, extended or elongate vapor bubble 16, as schematically indicated in FIG. 5b. A channel-like bubble formation may be generated also when laser energy is delivered to a tubular cavity. On the other hand, when highly absorbed laser energy is delivered into a liquid 3 through an immersed conical output surface 13, or a flat output surface 11 of sufficient small diameter D compared to the beam diameter d, or when weakly absorbed laser energy is delivered in "non-contact" mode and focused within the liquid 3 as described above, a generally spherical vapor bubble 18 develops, as schematically indicated in FIG. 5a. It is to be appreciated, however, that in reservoirs with a small containment factor (γ), the bubble's shape will be influenced more by the reservoir's geometry, and less by the fiber tip's output surface.

It is also to be appreciated that with shock waves generated according to present invention, conically shaped tips may get more quickly damaged during the violent shock wave emission, and therefore it may be advantageous to use flat surface fiber tips with the present invention.

Moreover, it is to be appreciated, that when in certain embodiments a weakly absorbed laser beam is delivered to a liquid 3 in a non-contact manner, and the beam's focus is located within the liquid 3, and away from the liquid surface, no bubble gets formed at or near the liquid's surface. Instead, the beam gets transmitted deeper into the liquid, and providing that the pulse duration is sufficiently short (≤100 ns), and the power density at the focal point within the liquid is sufficiently high, a bubble 18 is generated only when the laser beam 5 reaches its focal point deeper within the liquid 3.

Figure 6:
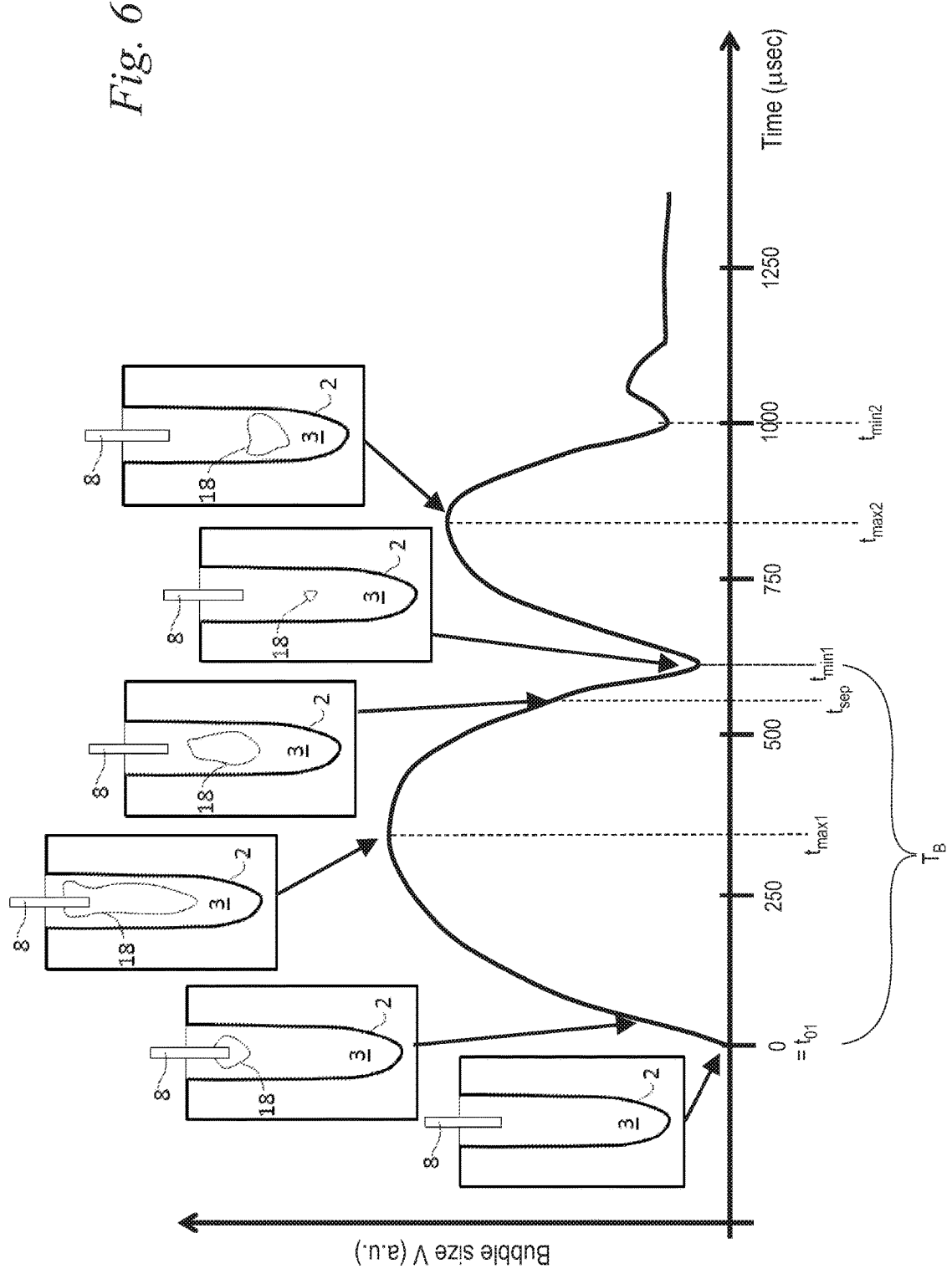
FIG. 6 illustrates an exemplary vapor bubble oscillation sequence under influence of one short laser pulse.
Figure 7:
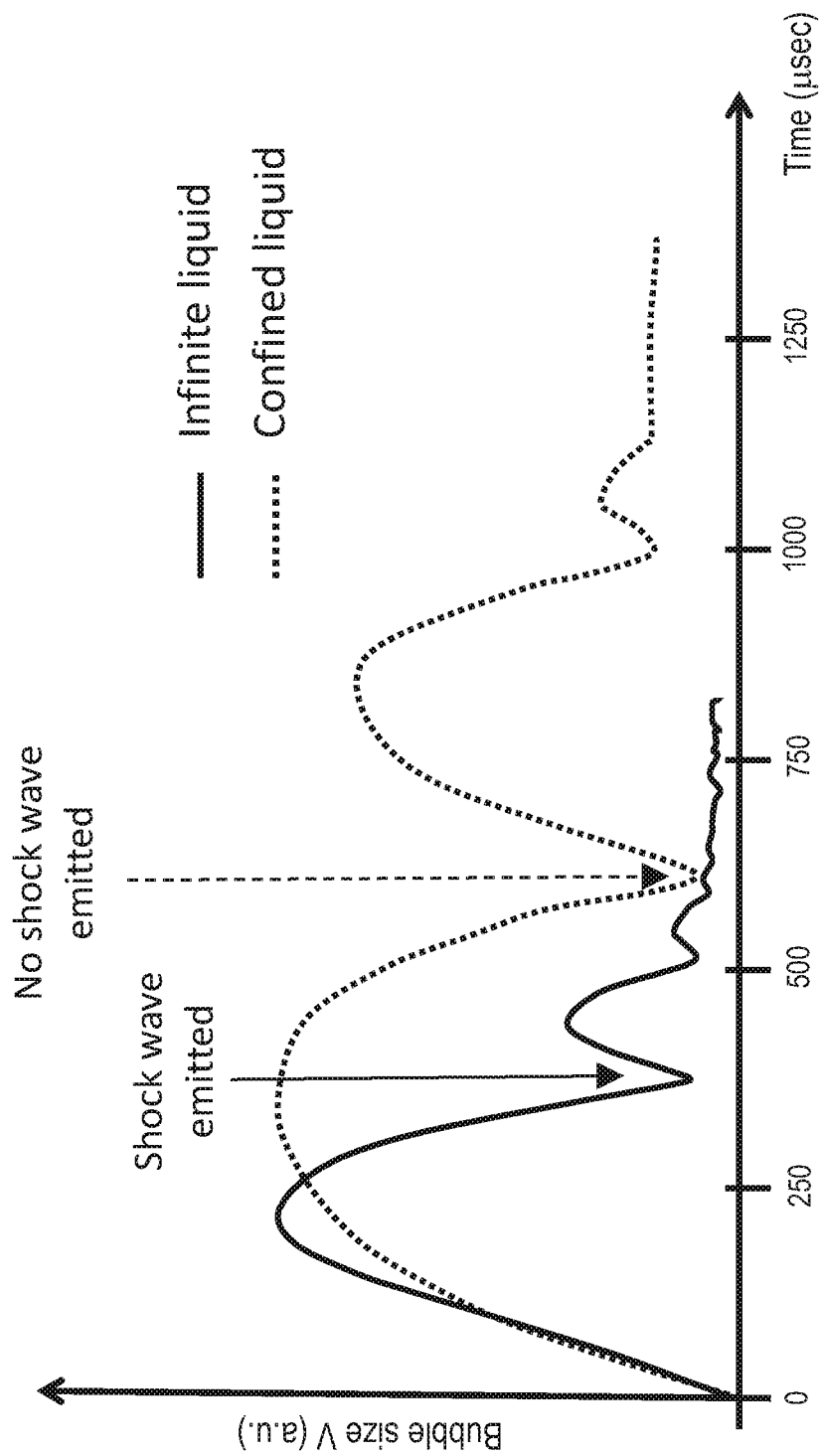
FIG. 7 illustrates the difference in single laser pulse vapor bubble oscillation sequence in an infinite and confined cylindrical liquid reservoir.

Turning now to FIG. 6, in various embodiments, the system utilizes an improved scientific understanding of the interaction of pulsed laser light with a highly absorbing liquid 3. When one pulse p of a pulsed laser beam 5 is delivered to such a liquid 3 at an onset time $t_{01}$, a bubble oscillation sequence develops. In the 1st phase of the bubble oscillation sequence (from time $t_{01}$ to time $t_{max1}$), laser energy deposition into the liquid 3 via absorption causes superheating of the liquid 3, and boiling induces a vapor bubble 18. The vapor bubble 18 expands rapidly, and thereafter reaches its maximum size at $t_{max1}$, when the internal pressure matches the pressure in the surrounding liquid 3.

In the $2^{nd}$ phase (from time $t_{max1}$ to time $t_{min1}$), the internal pressure is lower than the pressure in the surrounding liquid 3, and this difference in pressures forces the vapor bubble 18 to collapse.

When the vapor bubble 18 collapse completes at time $t_{min1}$, a rebound occurs thereafter, and the vapor bubble 18 starts to grow again up until time $t_{max2}$. This $3^{rd}$ phase (from time $t_{min1}$ to time $t_{max2}$) is followed again by a collapse in the $4^{th}$ phase (from time $t_{max2}$ to time $t_{min2}$). This oscillation process of the vapor bubble 18 continues, decreasing in amplitude and temporal period each time as illustrated in FIG. 6.

In various embodiments, a temporal bubble oscillation period $T_B$ may be defined as the time between $t_{01}$ and $t_{min1}$. Temporal bubble oscillation period $T_B$ varies based at least in part on the thermo-mechanical properties of the liquid 3, the shape and volume of the liquid 3 reservoir, the laser beam 5 emission profile, pulse duration, pulse energy, and so forth. Specifically, when the liquid 3 medium is contained in a root canal, e.g. in a body cavity 2 as shown in FIGS. 2a, 2b 3a, 3b, and 5, the bubble's oscillation period $T_B$ is prolonged, the bubble's collapse is slowed down, and no shock wave is emitted.

The exemplary bubble dynamics shown in FIG. 6 represents a bubble dynamics as measured in a cylindrical model of a root canal. A LightWalker branded laser system available from Fotona, d.o.o., Slovenia was used in the measurement. The liquid 3 within the cavity 2 was water, and the laser source 4 was an Er:YAG laser with the wavelength of 2940 nm which is strongly absorbed in water. The laser pulse duration was about 100 μsec and the laser pulse energy was about 20 mJ. The laser beam 5 was delivered from the laser source 4 through the Fotona Optoflex® brand articulated arm 14 and the handpiece 7 (Fotona H14) to a water filled model of a root canal cavity 2 through a flat fiber tip 24 (Fotona Varian 400) with its flat surface ending 11 submersed in water to a depth of 3 mm. The fiber tip's diameter was 0.4 mm, and the lateral diameter of the cylindrical model of a root canal was $d_r$=2 mm. A typical maximal bubble dimension in the lateral direction of the cylindrical root canal model was about $d_b$=1.5 mm, resulting in an approximate containment factor of $\gamma=d_r/d_b$=1.33. It is to be appreciated that because of this small containment factor, no shock waves were observed when the bubble 18 imploded at $t=t_{min1}$.

For comparison, FIG. 7 shows a measured bubble dynamics (full line) obtained in a large water reservoir, together with a measured bubble dynamics (dotted line) in a confined root canal model as already previously shown in FIG. 6. The same laser parameters and delivery system as described above were used for both liquid reservoir geometries. In the large reservoir, e.g. in a free liquid geometry, bubble oscillations can be accommodated by displacing the liquid at long distances, and therefore the oscillations were faster, with a bubble period $T_B$ being about two times shorter than in the root canal model. More importantly, in the free reservoir, shock wave emission was present during the bubble's collapse.

In the confined root canal model, a free expansion of the bubble laterally is not possible, and hence the water is pushed forward and backward in the root canal. Since the water obstructs the expansion of the vapor in the forward direction, the bubble grows backwards along the fiber, as can be seen from the insert in FIG. 6 at time $t_{max1}$. The pressure inside the bubble remains high for a long time, since it has to fight against the resistance of the water which has to be displaced in the small canal. This process delays the dynamics of expansion and implosion compared to a free water situation. In the root canal, the lateral and forward bubble expansion is limited by the root canal wall, while the backward expansion is blocked by the fiber making the lumen of the canal even smaller. These differences with a free water situation result in a measured approximately two times longer bubble oscillation time $T_B$ in the root canal as compared to a large reservoir. Also, no shock wave emission was detected during single pulse experiments in the confined root canal geometry.

Figure 8A:
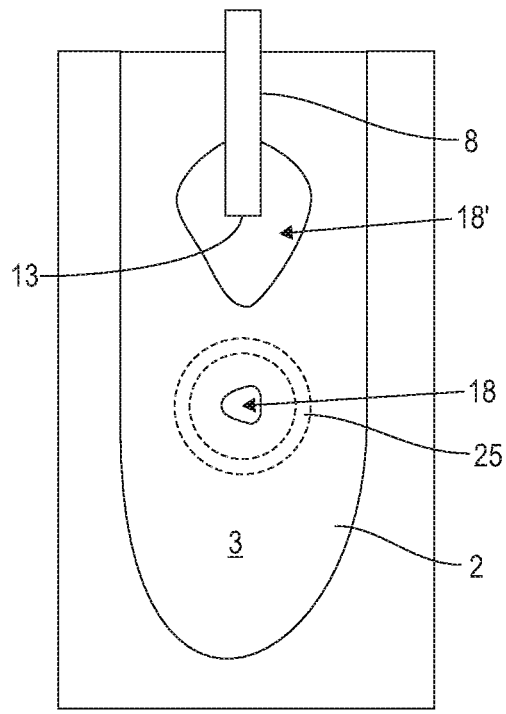
FIG. 8a illustrates an exemplary collapse and shock wave emission of a vapor bubble under the influence of an expanding subsequent bubble in confined reservoir, according to the present invention.
Figure 8B:
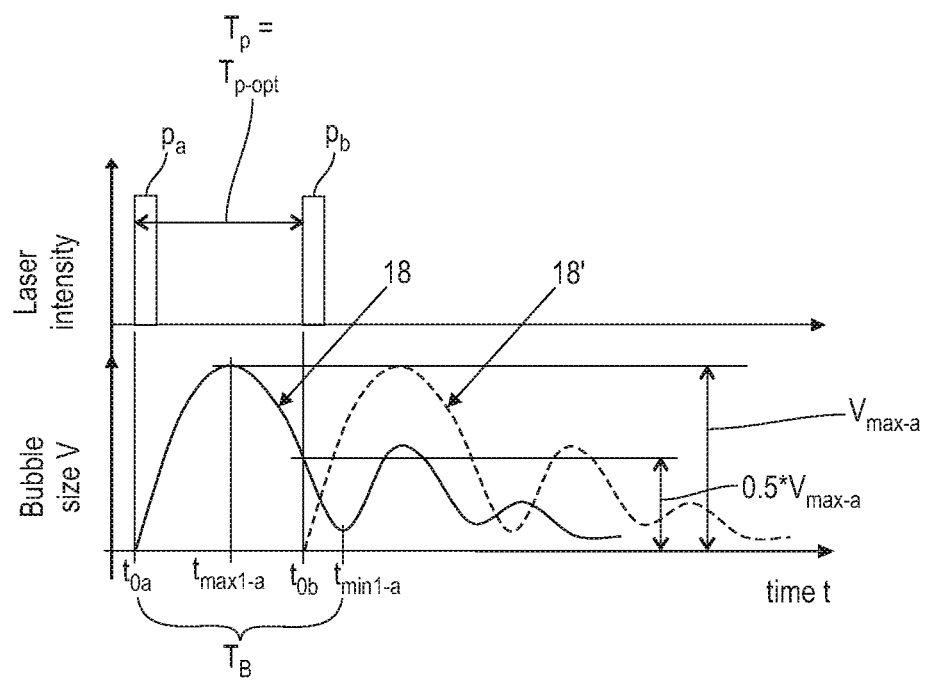
FIG. 8b illustrates an exemplary sequence of laser pulses, and exemplary development of vapor bubbles and emission of a shock wave, according to the present invention.

It is to be appreciated that the bubble implosion begins near the fiber tip where the expansion started, resulting in a separation of the bubble 18 from the fiber, as can be seen from the insert in FIG. 6 at time $t_p$. Referring now to FIG. 8a and FIG. 8b, according to present invention, at first a first laser pulse $p_a$ and then a second laser pulse $p_b$ with the same characteristics as the prior laser pulse $p_a$ is delivered into the root canal model at the respective onset times $t_{0a}$ and $t_{0b}$ with a pulse repetition time $T_p$ in between such that the second bubble 18' starts to expand at a time when the prior bubble 18 has already contracted to a certain size. This leads to a violent implosion of the prior bubble 18, and consequently to an emission of a shock wave 25 by the prior bubble 18 at the time of its collapse.

The foregoing oscillation dynamics of vapor bubbles 18 and 18' and associated relation to shock wave emission, facilitate the improved inventive system for and methods of treatment utilizing delivery of laser pulses p, for example treatment of root canals, drilled bone, and/or the like anatomical cavities 2 preferably with containment ratios $\gamma$<3, and even more preferably with containment factors $\gamma$<2. Moreover, and referring now to FIGS. 8a, 8b, in various embodiments, shock wave emission can be facilitated or enhanced in confined geometries preferably with containment ratios $\gamma$<3, and even more preferably with containment factors $\gamma$<2, and/or in highly viscous liquids by delivering a minimum of two laser pulses $p_a$, $p_b$ in a sequence whereas the pulse repetition time $T_p$ between the two pulses p in a sequence is such that the subsequent bubble 18' resulting from a subsequent pulse $p_b$ starts substantially expanding at a time when the prior bubble 18 resulting from a preceding laser pulse $p_a$ has contracted during the $2^{nd}$ phase (from time $t_{max1}$ to time $t_{min1}$) to a certain below defined size. It is to be appreciated that illustrations in FIGS. 8a, 8b are made only for the purposes of describing the invention, and do not necessarily depict amplitudes and shapes of laser pulses, bubble volumes or shock waves, as would be observed in actual embodiments of the invention.

It is to be appreciated that without the below described inventive double pulse set, no shock wave is emitted in confined liquid geometries, as shown in FIGS. 6 and 7. On the other hand, FIG. 8b shows the inventive laser pulse sequence with pulse durations $t_p$ and inventive pulse repetition time $T_p$, and the resulting dynamics of the resulting vapor bubbles and shock wave emissions. Individual pulses $p_a$ and $p_b$ within one sequence follow each other by a pulse repetition time $T_p$ The first pulse $p_a$ starts at an onset time $t_{0a}$ and generates, starting at the same onset time $t_{0a}$, a first vapor bubble 18. The size or volume V of the vapor bubble 18 oscillates in an expansion phase from a minimal volume at the first $t_{0a}$ to a maximal volume $V_{max-a}$ at a maximum volume time $t_{max1-a}$, and in a subsequent contraction phase from a maximal volume $V_{max-a}$ at the maximal volume time $t_{max1-a}$ to a minimal volume at a minimum volume time $t_{min1-a}$. When within the inventive pulse sequence the pulse repetition time $T_p$ is adjusted to match $T_{p-opt}$, in other words adjusted such that an onset time $t_{0b}$ of the subsequent laser pulse $p_b$ is delivered at about the time when the first vapor bubble 18 formed by the prior laser pulse $p_a$ has collapsed within ist first contraction phase to a size in a range from about $0.7 \times V_{max-a}$ to about $0.1 \times V_{max-a}$, preferably in a range from about $0.5 \times V_{max-a}$ to about $0.1 \times V_{max-a}$, expediently in a range from about $0.5 \times V_{max-a}$ to about $0.2 \times V_{max-a}$, and according to FIG. 8b of $0.5 \times V_{max-a}$ as a preferred example, two effects happen in parallel: As a first effect the first bubble 18 has separated from the exit component 8 and moved away downwards (FIG. 8a), in consequence of which although the exit component 8 has not moved the second pulse $p_b$ is introduced at a location different to the location where the first vapor bubble 18 is now present at the time of introducing the second laser pulse $p_a$, thereby generating the second vapor bubble 18' within the liquid 3. As a second effect the liquid pressure exerted on the collapsing prior bubble 18 by the expanding subsequent bubble 18', i.e., the bubble resulting from the subsequent laser pulse $p_b$, forces the prior bubble 18 to collapse faster, thus enabling or enhancing the emission of a shock wave 25 by the prior bubble 18, as indicated in FIG. 8a. The inventive pulse repetition time $T_p$ ensures that when the subsequent bubble starts substantially expanding i) the prior bubble is already in the fast collapse phase, and is therefore sensitive to the sudden additional pressure caused by the expanding subsequent bubble; and ii) in embodiments with a contact delivery of the laser energy into a liquid, the prior bubble has already substantially separated and moved away from the exit component 8, and therefore the laser energy of the subsequent laser pulse does not get absorbed within the prior bubble. However, in any case where the created vapor bubbles 18, 18' have no sufficient tendency to separate from the exit component or to otherwise change their location, and also in embodiments with a non-contact delivery, the exit component 8 or laser focal point may be spatially moved in between the pulses, for example by a scanner, in order to avoid the laser energy of the subsequent laser pulse $p_b$ to be absorbed within the prior bubble 18.

It is to be appreciated that the invention is not limited to the emission of only two subsequent pulses within a pulse set. A third pulse following a second laser pulse, and fulfilling both conditions, may be delivered resulting in an emission of a shock wave by the previous (second) bubble. Similarly, an $n^{th}$ subsequent laser pulse will result in an emission of a shock wave by the $(n-1)^{th}$ bubble, and so on as further laser pulses are being added to the set of pulses. More laser pulses are delivered in one pulse set higher is the laser-to-shock wave energy conversion, with the energy conversion efficiency being proportional to the ratio $(n-1)/n$ where n is the total number of laser pulses delivered in one pulse set 21 (FIG. 10).

FIG. 9 shows in a schematic diagram the temporal course of the pulse sets 21 according to the invention. In this connection, the course of the amplitude of the pulse sets 21 is illustrated as a function of time. The pulse sets 21 follow one another along one single optical path within the laser system 1 with a temporal pulse set spacing $T_S$ being the temporal difference between the end of one pulse set 21 and the beginning of the next pulse set 21. The temporal pulse set spacing $T_S$ is expediently 10 ms≤$T_S$≤500 ms, advantageously 10 ms≤$T_S$≤100 ms, and is in the illustrated embodiment of the inventive method approximately 10 ms. The lower temporal limit for temporal set spacing $T_S$ of 10 ms is set in order to allow sufficient time for the laser active material, such as, for example, a flash-lamp pumped laser rod, to cool off during the time between subsequent pulse sets 21. The individual pulse sets 21 have a temporal set length $t_S$ of, for example, approximately 2 ms. Depending on the number of individual pulses p provided infra the value of the temporal set length $t_S$ can vary. The maximal number of pulse sets 21, and correspondingly the maximal number of individual pulses p, that may be delivered during a treatment is limited at least by the maximal delivered cumulative energy below which the temperature increase of the liquid 3 does not exceed an allowed limit.

FIG. 10 shows an enlarged detail illustration of the diagram according to FIG. 9 in the area of an individual pulse set 21. Each pulse set 21 has expediently at least two and maximally 20 individual pulses p, advantageously two to eight individual pulses p, and preferably two to four individual pulses p, and in the illustrated embodiment according to FIG. 10 there are six individual pulses p. Maintaining the aforementioned upper limit of the number of individual pulses p per pulse set 21 avoids overheating of the laser active material. The individual pulses p have a temporal pulse duration $t_p$ and follow one another along one single optical path within the laser system in a pulse repetition time $T_p$, the pulse repetition time $T_p$ being the time period from the beginning of one single pulse p to the beginning of the next, subsequent pulse p.

The pulse duration $t_p$ is for weakly absorbed wavelengths in the range of ≥1 ns and <85 ns, and preferably ≥1 ns and ≤25 ns. The lower temporal limit of the pulse duration $t_p$ for weakly absorbed wavelengths ensures that there are no shock waves created in the liquid 3 during the vapor bubble 18 expansion. And the upper pulse duration $t_p$ limit for weakly absorbed wavelengths ensures that the laser pulse power is sufficiently high to generate optical breakdown in the liquid.

For highly absorbed wavelengths, the pulse duration $t_p$ is in the range of ≥1 µs and <500 µs, and preferably of ≥10 µs and <100 µs. The lower temporal limit for highly absorbed wavelengths ensures that there is sufficient pulse energy available from a free-running laser. And the upper pulse duration limit for highly absorbed wavelengths ensures that the generated heat does not spread via diffusion too far away from the vapor bubble, thus reducing the laser-to-bubble energy conversion efficiency. Even more importantly, the upper pulse duration limit ensures that laser pulses are shorter than the vapor bubble rise time, $t_{max1} t_{01}$, in order not to interfere with the bubble temporal oscillation dynamics. In FIG. 10, the amplitude of the laser beam or of its individual pulses p is schematically plotted as a function of time wherein the temporal course of the individual pulses p, for ease of illustration, are shown as rectangular pulses. In practice, the pulse course deviates from the schematically shown rectangular shape of FIG. 10.

In order to facilitate improved adjustability and/or control, in various embodiments the laser system 1 is configured with a laser source 4 having a variable pulse rate, variable pulse set rate, and/or variable temporal pulse set length $t_S$ of the pulse set 21. In this manner, the shock wave emission may be optimized for a particular anatomical cavity 2 dimensions and shape, and also for a particular placement of the fiber tip or positioning of the laser focus in the different locations relative to the cavity. Namely, the placement of the fiber tip or positioning of the laser focus relative to the cavity may affect the properties of the bubble oscillations and shock wave emission. In one of the embodiments, a centering system may be used to center the fiber tip relative to the walls of the cavity, or to center the fiber tip near the entrance, or bottom of the cavity, or near an occlusion within the cavity.

The pulse repetition time $T_P$ is, according to the invention, in the range between approximately 75% $T_B$ and approximately 90% $T_B$. The bubble oscillation period $T_B$ may vary from about 100 µs to about 1000 µs, based at least in part on the thermo-mechanical properties of the liquid 3, the shape and volume of the liquid reservoir, the laser wavelength, beam emission profile, configuration of the treatment head, and so forth. Accordingly, when the pulse repetition time $T_P$ will be adjusted to approximately match $T_{p\text{-}opt}$, the pulse repetition rate $F_P$, will be in the range from about 1,1 kHz to about 13,3 kHz.

The laser pulse energy $E_L$, according to the invention, may be fixed for all pulses within a pulse set 21. In certain embodiments, however, the energy of the subsequent the pulse energy may be adjustable to automatically gradually decrease, for example linearly or exponentially, from pulse p to pulse p within each set 21. This approach may be especially advantageous for pulse sets with a pulse number of n=2, where the energy $E_L$ of the second pulse $p_b$ may be lower than that of the first pulse $p_a$, since the function of the second bubble 18' is only to create an additional pressure on the collapsing bubble 18 during the initial expansion phase of the bubble 18'.

Alternatively, the laser pulse energy $E_L$ may be adjustable to gradually increase from pulse to pulse within a pulse set 21, in order to increase even further the pressure of the subsequent bubbles on the prior bubbles.

In one of the embodiments of our invention, the laser system comprises a feedback system 9 to determine a bubble oscillation dimension or amplitude of the prior vapor bubble generated within the liquid. Furthermore, the laser system comprises adjusting means for adjusting the pulse repetition time $T_p$ to achieve at least approximately that the subsequent bubble 18', i.e., the bubble 18' generated by the subsequent laser pulse $p_b$, starts to expand when the volume of the prior bubble 18 has already contracted to the desired size as described above. The feedback system 9 preferably comprises an acoustical, a pressure, or an optical measurement sensor for sensing the bubble size V. As a result of the bubble oscillation sensing, the laser pulse repetition time $T_p$ might be manually adjusted by the user to be approximately equal to $T_{p\text{-}opt}$. However, in a preferred embodiment, the feedback system and the adjusting means are connected to form a closed control loop for automatically delivering a subsequent laser pulse at the moment when the feedback system has detected that the size of the prior bubble has contracted to the required size, that is at an adjusted pulse repetition time $T_P = T_{p\text{-}opt}$ (FIG. 8b). In either case of manual or closed loop control adjustment the number of pulses p within one sequence is not limited to one first and one second pulse $p_a$, $p_b$. It may also be advantageous, that multiple pulses $p_0$ to $p_n$, $p_{n+1}$ of FIG. 10 within one pulse sequence 21 may follow one another at a certain adjusted pulse repetition time $T_P = T_{p\text{-}opt}$, as exemplarily shown in the left portion of FIG. 8b between two adjusted pulses $p_a$, $p_b$. In such case, every individual pulse $p_0$ to $p_n$, serves as a first pulse $p_a$ of FIG. 8, while every individual pulse $p_1$ to $p_{n+1}$ serves as a second pulse $p_b$ of FIG. 8 for augmenting the shock wave generation with the first bubble 18 related to the preceding first pulse $p_a$.

In yet another embodiment, and in order to facilitate automatic adjustability of the pulse repetition time $T_p$ to any geometric confinement conditions or liquid thermo-mechanical characteristics without the need for a feedback, the laser system 1 is configured with a laser source 4 having an automatically variable, "sweeping" pulse generation. In this manner, the shock wave emission may be automatically optimized for a particular anatomical cavity 2 dimensions and shape. The general idea of the inventive sweeping technique is to generate multiple pairs of first and second bubbles 18, 18' without the aid of feedback such, that the time difference between the onset time $t_{0b}$ of the second vapor bubble 18' and the onset time $t_{0a}$ of the first vapor bubble 18 (FIG. 8b) is repeatedly varied in a sweeping manner. By varying said time difference it is made sure, that at least one pair of bubbles 18, 18' matches the required timing, as with the first and second bubbles 18, 18' of FIG. 8b, and thus emitting at least one shock wave 25 (FIG. 8a) during each sweeping cycle. By repeatedly performing such sweeping cycles, the generation of shock waves 25 may be repeated to an extent until the desired irrigation goal is achieved.

Referring now to FIG. 10, a first inventive shock wave emission enhancing pulse (SWEEP) set 21 is proposed, wherein the pulse repetition time $T_P$ is varied or "swept" in discreet positive or negative steps Δ, preferably across a range from 75 μsec to 900 μsec (or from 900 μsec to 75 μsec in the case of a negative Δ), even more preferably across a range from 300 μsec to 600 μsec (or from 600 μsec to 300 μsec in the case of a negative Δ), and expediently across a range from 350 μsec to 550 μsec (or from 550 μsec to 350 μsec in the case of a negative Δ). By using this inventive pulse repetition sweeping technique, it is ensured that at least one pair of pulses p within the number of multiple pulses $p_0$ to $p_n$, $p_{n+1}$ of FIG. 10 matches the required pulse repetition rate, thereby resembling the first and second pulses $p_a$, $p_b$ of FIG. 8b with the required adjusted and optimal pulse repetition time $T_P = T_{p\text{-}opt}$ in between, and thus generating at least one fitting pair of bubbles 18, 18' (FIG. 8b) for emitting at least one shock wave during each sweeping cycle.

The pulse repetition time $T_P$ may be "swept" within each pulse set 21 as exemplarily shown in FIG. 10 where the pulse repetition time $T_p$ is discretely swept from pulse $p_0$ to pulse $p_{n+1}$ by changing the pulse repetition time $T_p$ from pulse to pulse by an additional discreet temporal step Δ, while multiple pulse sets 21 of such or similar kind may follow one another. In the illustrated embodiment of the inventive method, pulse sets 21 consisting of six pulses $p_0$ to $p_{n+1}$ are shown, but pulse sets 21 with a larger or smaller number of pulses p may be used as well.

Alternatively, as a second preferred sweeping pattern, a number of m pulse sets 21 may be applied, wherein the pulse repetition time $T_P$ may be varied or "swept" from pulse set 21 to pulse set 21 as exemplarily shown in FIG. 11: The pulse repetition time $T_p$ is discretely swept from pulse set 21 to pulse set 21 by starting at an initial repetition time $T_{p0}$, and then changing the pulse repetition time $T_p$ from pulse set 21 to pulse set 21, by a discreet temporal step Δ to a final repetition time $T_{pm}$. The sweeping cycle may be re-started each time the whole sweeping range has been covered. In the embodiment of the inventive method illustrated in FIG. 11, pulse sets consisting of two pulses $p_0$, $p_1$ are shown, but pulse sets with a larger number of pulses p may be used as well. In any case the same effect as with the sweeping pattern of FIG. 10 can be achieved: At least one pair of pulses $p_0$, $p_1$ within the number of m pulse sequences 21 of FIG. 11 matches the required pulse repetition rate, thereby resembling the first and second pulses $p_a$, $p_b$ of FIG. 8b with the required adjusted and optimal pulse repetition time $T_P = T_{p\text{-}opt}$ in between, and thus emitting at least one shock wave during each sweeping cycle.

Figure 12:
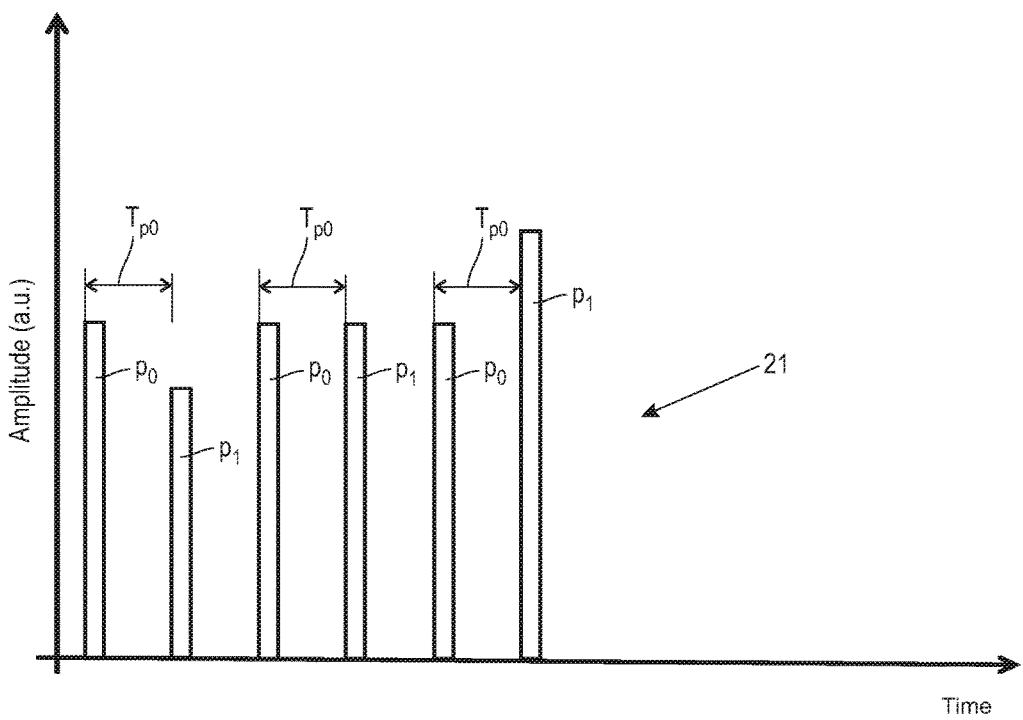
FIG. 12 represents an enlarged diagrammatic illustration of a detail of an alternative pulse set according to FIG. 9 with the temporal course of individual pulses with sweeping pulse energy from pulse to pulse within one pulse set.

A further preferred, third sweeping pattern is schematically depicted in FIG. 12: One pulse set 21 contains multiple pairs of two pulses $p_0$, $p_1$, wherein a subsequent pulse $p_2$ of each pair follows a corresponding initial pulse $p_1$, and wherein the pulse repetition times $T_p$ within all pairs is kept constant. However, from pair of pulses $p_0$, $p_1$ to pair of pulses $p_0$, $p_1$ the pulse energy of each second pulse $p_1$ is varied in a sweeping manner. In the shown example the pulse energy is increased from pair to pair by a certain delta. On the other hand, an energy decrease may be applied as well. Such pulse energy sweeping is based on the finding, that the lower the second pulsed $p_1$ energy is, the longer it will take the second bubble 18' (FIG. 8a, 8b) to develop appreciably to influence the first bubble's 18 collapse, and vice versa. This way it can again be achieved, that at least one pair of bubbles 18, 18' matches the required timing, as with the first and second bubbles 18, 18' of FIG. 8b, and thus emitting at least one shock wave 25 (FIG. 8a) during each sweeping cycle. Alternatively, the pulse energy of each second pulse $p_1$ may be varied in a sweeping manner from one pulse set 21 to the next pulse set 21.

A combined SWEEP method may be used as well, where the pulse repetition time $T_P$ is "swept" within pulse sets 21 from one pulse p to another, and also from pulse set 21 to pulse set 21. Furthermore, the sweeping pulse energy of FIG. 12 may be combined with the sweeping pulse repetition times $T_p$ of FIG. 10 and/or of FIG. 11.

In yet another embodiment, either with a sweeping pulse repetition time $T_P$ or not, the electromagnetic radiation system may be adjusted to generate and deliver multiple pairs of two pulses $p_0$, $p_1$, and wherein from pair of pulses $p_0$, $p_1$ to pair of pulses $p_0$, $p_1$ the pulse energy of each second pulse $p_1$ is reduced in comparison to the pulse energy of each first pulse $p_0$, preferably to a pulse energy which is just sufficiently high to trigger an emission of a shock wave by the bubble generated by a first pulse $p_0$, but not much higher. In this manner, the energy of a second pulse $p_1$ remaining to be delivered by a second pulse $p_1$ after a shock wave by a first pulse $p_0$ has already been emitted, is not wasted for, for example, unnecessary heating of the cavity. The ratio of the pulse energy of the second pulse $p_1$ to the pulse energy of the first pulse $p_0$, may be in a range from 0.8 to 0.1, preferably in a range from 0.6 to 0.1, and expediently in a range from 0.5 to 0.2.

And in yet another embodiment, either with a sweeping pulse repetition time $T_P$ or not, the electromagnetic radiation system may be adjusted to generate and deliver multiple pairs of two pulses $p_0$, $p_1$, and wherein from pair of pulses $p_0$, $p_1$ to pair of pulses $p_0$, $p_1$ the pulse duration of each second pulse $p_1$ is shorter in comparison to the pulse duration of each first pulse $p_0$. For example, the pulse duration of each first pulse may be in a microseconds duration range, and the pulse duration of each second pulse may be in a nanoseconds duration range. In this manner, an emission of a shock wave by a bubble generated by a first pulse $p_1$ shall occur faster and more readily. Alternatively, the pulse duration of each second pulse $p_1$ may be longer in comparison to the pulse duration of each first pulse $p_0$, in order to make the exact timing of the pulses (in terms of the pulse repetition time $T_p$) less critical.

In summary and opposite to the prior art pulse sequence and vapor bubble formation, when the inventive synchronization is applied, the bubble's shock wave emission following each prior laser pulse is enhanced by the bubble's energy from the subsequent pulse. As a result, the cleaning efficacy of liquid filled cavities is substantially improved.

One of the methods that is claimed is a method for irrigation, including debriding, cleaning and decontamination, of a dental root canal (2) filled with liquid (3), such as water or another irrigant, comprising of the following steps:
  providing a laser system (1) comprising a laser source (4) for generating a laser beam (5), an optical delivery system (6), a treatment handpiece (7) including an exit component (8), and adjusting means (10), wherein the treatment handpiece (7) and its exit component (8) are configured to irrigate the anatomical cavity (2) in a contact manner, wherein a wavelength of the laser beam (5) is in a range from above 1.3 µm to 11.0 µm inclusive, wherein the laser system is adapted to be operated in pulsed operation with pulse sets (21) containing at least two and maximally twenty individual pulses (p) of a temporally limited pulse duration ($t_p$), wherein the repetition time (t) between the pulse sets is ≥10 ms, and wherein the individual pulses (p) follow one another with a fixed pulse repetition time ($T_P$) within a range of 200 µs, inclusive, to 450 µs, inclusive;
  applying said pulsed laser beam (5) to the liquid (3) disposed within the anatomical cavity (2) to form at least one prior vapor bubble (18) and a at least one subsequent vapor bubble (18') in the liquid (3), in order to achieve at least one shock wave emitted by a prior vapor bubble (18).
  performing the treatment until desired cleaning, including debriding, irrigation and decontamination, is achieved.

In one of the embodiments, the treatment of an anatomical cavity may be performed until desired cleaning, including debriding, irrigation and decontamination, is achieved or until the average liquid's temperature rise within the anatomical cavity exceeds 3.5 degrees Celsius, whichever occurs first.

Alternatively, a SWEEP configuration may be used instead of a fixed pulse repetition time ($T_p$).

Several irrigants for the endodontic treatment are available, and include sodium hypochlorite (NaOCl), chlorhexidine gluconate, alcohol, hydrogen peroxide and ethylenediaminetetraacetic acid (EDTA). However, in one of the preferred embodiments only water may be used instead of a potentially toxic irrigant since the generation of shock waves according to our invention reduces or eliminates the need for the use of chemicals.

Preferably, the laser source 4 is an Er:YAG laser source having a wavelength of 2940 nm, wherein laser pulse energy is in a range from 1 mJ to 40 mJ, wherein the exit component 8 is cylindrical, having a diameter D between 200 µm and 1000 µm, wherein the conical output surface 13 has a conical half angle α being in the range from 16° to 38°, preferably from 34° to 38°, wherein the temporal separation $T_S$ between pulse sets 21 is <0.5 s, and wherein the cumulative delivered energy during a treatment is below 150 J.

Expediently, the laser system 1 is configured to generate coherent light having a wavelength highly absorbed in OH-containing liquids, by means of one of an Er:YAG laser source having a wavelength of 2940 nm, an Er:YSGG laser source having a wavelength of 2790 nm, an Er,Cr:YSGG laser source having a wavelength of 2780 nm or 2790 nm, and a $CO_2$ laser source having a wavelength of about 9300 to about 10600 nm, and wherein laser pulse energy is in a range from 1 mJ to 1000 mJ, preferably in a range from 1 mJ to 100 mJ.

It will be appreciated that, while the foregoing example methods are directed to treatment of root canals and/or bone cavities, in accordance with principles of the present disclosure, similar methods and/or systems may be utilized to treat other body tissues, for example periodontal pockets, and/or the like. The method may be also used to irrigate, debride and clean selected small surfaces of electronic and precision mechanical components during manufacturing, maintenance and servicing, especially when it is not desirable or possible to expose the whole electronic or other component to a standard cleaning or irrigation procedure.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure and may be expressed in the following claims.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims. Systems, methods and computer program products are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" is used in the claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

The invention claimed is:

1. A method for cleaning of cavities filled with a liquid using an electromagnetic radiation system, wherein the electromagnetic radiation system comprises a radiation source for generating a radiation beam and an optical delivery system for delivering the radiation beam, wherein the delivery system includes a treatment handpiece and an exit component, and wherein the method comprises the following steps:
   using the treatment handpiece and the exit component for irradiating the liquid within a cavity with the radiation beam,
   choosing a wavelength of the radiation beam for significant absorption of the radiation beam in the liquid, wherein significant absorption is absorption of electromagnetic radiation such that bubbles are generated within the liquid,
   operating the electromagnetic radiation system in pulsed operation with at least one pulse set containing at least two individual pulses, wherein a first pulse of the pulses is followed by a second pulse of the pulses with a pulse repetition time,
   generating a first vapor bubble within the liquid by means of the corresponding first pulse such, that the first vapor bubble oscillates in an expansion phase from a minimal volume to a maximal volume and in a subsequent contraction phase from a maximal volume to a minimal volume,
   generating a second vapor bubble within the liquid by means of the corresponding second pulse at a location different to the location where the first vapor bubble is present at the time of generating the second vapor bubble,
   adjusting the pulse repetition time such, that an onset time of the second vapor bubble is within the first contraction phase of the first vapor bubble, when the first vapor bubble has contracted from its maximal volume to a size in a range from about 0.7 to about 0.1 of the maximal volume.

2. The method according to claim 1,
wherein the electromagnetic radiation system is a laser system, wherein the radiation source is a laser source, wherein the radiation beam is a laser beam, and wherein the wavelength of the laser beam is in a range from above 0.4 µm to 11.0 µm inclusive.

3. The method according to claim 1,
wherein the pulse repetition time is adjusted such that the onset time of the second vapor bubble is within the first contraction phase of the first vapor bubble, when the first vapor bubble has contracted from its maximal volume to a size in a range from about 0.5 to about 0.1 times the maximal volume.

4. The method according to claim 1,
wherein within one pulse set the pulse repetition time is adjusted to be in a range from about 50 µs As to about 900 µs.

5. The method according to claim 1,
wherein the electromagnetic radiation system further comprises a feedback system and adjusting means, wherein a bubble oscillation intensity of at least one vapor bubble generated within the liquid when irradiated with the irradiation beam is determined by the feedback system, and wherein the pulse repetition time is adjusted by the adjusting means as a function of the determined bubble oscillation intensity.

6. The method according to claim 5,
wherein the feedback system and the adjusting means are connected to form a closed control loop for automatically adjusting the temporal pulse period.

7. The method according to claim 5,
wherein the feedback system comprises an acoustical, a pressure, or an optical measurement sensor for sensing the bubble oscillation intensity.

8. The method according to claim 1,
wherein multiple pairs of first and second bubbles are generated such, that the time difference between the onset time of the second vapor bubble and the onset time of the related first vapor bubble is repeatedly varied in a sweeping manner.

9. The method according to claim 8,
wherein multiple pulses are generated and delivered within one pulse set at a sweeping pulse repetition time, and wherein from pulse to pulse the pulse repetition time is varied in a sweeping manner.

10. The method according to claim 8,
wherein multiple pulse sets are generated and delivered, and wherein each pulse set contains at least two pulses, and wherein from pulse set to pulse set the repetition time between two subsequent pulses is varied in a sweeping manner.

11. The method according to claim 8,
wherein multiple pairs of two pulses are generated and delivered, and wherein from pair of pulses to pair of pulses the pulse energy of each second pulse is varied in a sweeping manner.

12. The method according to claim 1,
wherein two or more pulse sets are provided, and wherein a temporal separation between the pulse sets is ≥10 ms.

13. The method according to claim 1,
wherein one pulse set consists of two to twenty individual pulses.

14. The method according to claim 2,
wherein the wavelength of the laser beam is chosen to be in a range from about 1.3 μm to about 11.0 μm for the laser beam to be highly absorbed in the liquid, and wherein a pulse duration of one individual laser pulse is in the range of ≥1 μs and <500 μs.

15. The method according to claim 14,
wherein a laser source is one of an Er:YAG laser source having a wavelength of 2940 nm, an Er:YSGG laser source having a wavelength of 2790 nm, an Er,Cr:YSGG laser source having a wavelength of 2780 nm or 2790 nm, or a $CO_2$ laser source having a wavelength of 9300 to 10600 nm, and wherein a pulse energy of one individual laser pulse is in the range from 1 mJ to 1000 mJ.

16. The method according to claim 15,
wherein the laser source is an Er:YAG laser having a wavelength of 2940 nm, wherein the pulse energy of one individual laser pulse is in a range from 1.0 mJ to 40.0 mJ, wherein the temporal separation between two consecutive pulse sets is <0.5 s, and wherein the cumulative delivered energy during one treatment is <150 J.

17. The method according to claim 14,
wherein the handpiece and its exit component are adjusted for both a contact or a non-contact delivery of laser energy to the liquid within the cavity, and wherein the exit component has a flat output surface providing a generally parallel exiting beam portion of the laser beam.

18. The method according to claim 14,
wherein the handpiece and its exit component are adjusted for a contact delivery of laser energy to the liquid within the cavity, and wherein the exit component has a substantially conically shaped output surface providing a generally circumferentially spread exiting beam portion of the laser beam.

19. The method according to claim 14,
wherein the delivery system comprises an articulated arm through which the laser beam is delivered from the laser source to the exit component.

20. The method according to claim 14,
wherein the delivery system further comprises a scanner for scanning one of a flat shaped output surface and a conically shaped output surface of the exit component with the incoming laser beam.

21. The method according to claim 14,
wherein the handpiece and its exit component are adjusted for a non-contact delivery of laser energy to the liquid within the cavity, and wherein optical focusing means are provided to focus the exiting beam portion of the laser beam within the volume of the liquid.

22. The method according to claim 2,
wherein the wavelength of the laser beam is chosen to be in a range from about 0.4 μm to about 1.3 μm for the laser beam to be weakly absorbed in the liquid, and wherein the pulse duration of one individual laser pulse is in the range of ≥1 fs and <100 ns.

23. The method according to claim 22,
wherein the laser source is one of a Q-switched Nd:YAG laser source having a wavelength of 1064 nm, a Q-switched ruby laser source having a wavelength of 690 nm, or an alexandrite laser source having a wavelength of 755 nm, including laser sources with frequency doubled wavelengths of these laser sources, and wherein a pulse energy of one individual laser pulse is in the range from 0.05 mJ to 1000 mJ.

24. The method according to claim 3,
wherein the pulse repetition time is adjusted such that the onset time of the second vapor bubble is within the first contraction phase of the first vapor bubble, when the first vapor bubble has contracted from its maximal volume to a size in a range from about 0.5 to about 0.2 times the maximal volume.

25. The method according to claim 13,
wherein one pulse set consists of two to eight individual pulses.

26. The method according to claim 25,
wherein one pulse set consists of three to six individual pulses.

27. The method according to claim 14,
wherein the pulse duration of one individual laser pulse is in the range of ≥10 μs and <100 μs.

28. The method according to claim 15,
wherein a pulse energy of one individual laser pulse is in the range from 1 mJ to 100 mJ.

29. The method according to claim 16,
wherein the pulse energy of one individual laser pulse is in a range from 5.0 mJ to 20.0 mJ.

30. The method according to claim 22,
wherein the pulse duration of one individual laser pulse is in the range of ≥1 ns and <25 ns.

* * * * *